US008063232B2

(12) United States Patent
Hagadorn et al.

(10) Patent No.: US 8,063,232 B2
(45) Date of Patent: Nov. 22, 2011

(54) METATHESIS CATALYST AND PROCESS FOR USE THEREOF

(75) Inventors: John R. Hagadorn, Houston, TX (US); Matthew W. Holtcamp, Huffman, TX (US); Matthew S. Bedoya, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/939,054

(22) Filed: Nov. 3, 2010

(65) Prior Publication Data

US 2011/0112305 A1    May 12, 2011

Related U.S. Application Data

(60) Provisional application No. 61/259,514, filed on Nov. 9, 2009.

(51) Int. Cl.
*C07D 207/04* (2006.01)
(52) U.S. Cl. .................................. 548/402; 548/400
(58) Field of Classification Search .............. 548/400, 548/402
See application file for complete search history.

(56) References Cited

U.S. PATENT DOCUMENTS

| | | | |
|---|---|---|---|
| 6,900,347 | B2 | 5/2005 | Paulson et al. |
| 7,119,216 | B2 | 10/2006 | Newman et al. |
| 7,205,424 | B2 | 4/2007 | Nolan |
| 7,268,242 | B2 | 9/2007 | Pederson et al. |
| 7,312,331 | B2 | 12/2007 | Bertrand et al. |
| 7,632,772 | B2 | 12/2009 | Zhan |
| 2005/0070750 | A1 | 3/2005 | Newman et al. |
| 2006/0287450 | A1 | 12/2006 | Kohler et al. |
| 2007/0043180 | A1 | 2/2007 | Zhan |
| 2007/0270621 | A1 | 11/2007 | Millis et al. |
| 2008/0027194 | A1 | 1/2008 | Schrodi |
| 2008/0064891 | A1 | 3/2008 | Lee |
| 2008/0269525 | A1 | 10/2008 | Bertrand et al. |
| 2009/0048459 | A1 | 2/2009 | Tupy et al. |
| 2009/0069516 | A1 | 3/2009 | Obrecht et al. |
| 2009/0187035 | A1 | 7/2009 | Ko et al. |
| 2009/0259065 | A1 | 10/2009 | Abraham et al. |

FOREIGN PATENT DOCUMENTS

| | | |
|---|---|---|
| EP | 2 151 446 | 2/2010 |
| JP | 58-154594 | 9/1983 |
| WO | WO 00/71554 | 11/2000 |
| WO | WO 2004/062763 | 7/2004 |
| WO | WO 2006/138166 | 12/2006 |
| WO | WO 2008/010961 | 1/2008 |
| WO | WO 2008/046106 | 4/2008 |
| WO | WO 2008/095785 | 8/2008 |
| WO | WO 2008/125568 | 10/2008 |
| WO | WO 2008/140468 | 11/2008 |
| WO | WO 2009/009597 | 1/2009 |
| WO | WO 2009/126831 | 10/2009 |

OTHER PUBLICATIONS

Alder et al., "Complexation of Stable Carbenes With Alkali Metals", Chemical Communications, 1999, No. 3, pp. 241-242.
Anderson et al., "Synthesis and Reactivity of Olefin Metathesis Catalysts Bearing Cyclic (Alkyl)(Amino)Carbenes", Angewandte Chemie, International Edition, 2007, vol. 46, No. 38, pp. 7262-7265.
Anderson et al., "Kinetic Selectivity of Olefin Metathesis Catalysts Bearing Cyclic (Alkyl)(Aminoi)Carbenes", Organometallics, 2008, vol. 27, No. 4, pp. 563-566.
Arduengo III et al., "Carbene-Lithium Interactions", Chemistry Letters, 1999, vol. 28, No. 10, pp. 1021-1022.
Arduengo et al., "Carbene Adducts of Magnesium and Zinc", Journal of Organometallic Chemistry, 1993, vol. 462, No. 1-2, pp. 13-18.
Arduengo et al., "Adducts of Carbenes with Group II and XII Metallocenes, Organometallics, 1998, vol. 17, No. 15, pp. 3375-3382.
Arnold et al., "Magnesium and Zinc Complexes of Functionalised, Saturated N-heterocyclic Carbene Ligands: Carbene lability and Functionalisation, and Lactide Polymerisation Catalysis", Journal of Chemical Society, Dalton Transactions, 2009, No. 35, pp. 7236-7247.
Arrowsmith et al., "AHydride-Rich Magnesium Cluster", Angewandte Chemie, International Edition, 2009, vol. 48, No. 22, pp. 4013-4016.
Azizoglu et al., "Substituent Effects on the Ring-Opening Mechanism of Lithium Bromocyclopropylidenoids to Allenes", Journal of Organic Chemistry, 2008, vol. 73, No. 21, pp. 8182-8188.
Berthelot et al., "Gas-Phase Reactivity of (C5H5Mg)+ Complexes: An Experimental and Theoretical Study", Journal of Physical Chemistry. A molecules, Spectroscopy, Kinetics, Enironment and General Theory, 1998, vol. 102, No. 29, pp. 6025-6034.
Bourisson et al., "Stable Carbenes", Chemical Reviews, 2000, vol. 100, No. 1, pp. 39-91.
Burdett et al., "Renewable Monomer Feedstocks via Olefin Metathesis: Fundamental Mechanistic Studies of Methyl Oleate Ethenolysis with the First-Generation Grubbs Catalyst", Organometallics, 2004, vol. 23, No. 9, pp. 2027-2047.
Diez-Gonzalez et al., "N-Heterocyclic Carbenes in Late Transition Metal Catalysis", Chemical Reviews, 2009, vol. 109, No. 8, pp. 3612-3676.
Dragutan et al., "Ruthenium Indenylidene Complexes: Metathesis Catalysts With Enhanced Activity", Platinum Metals Rev. 2005, vol. 49, Issue 1, p. 33-40.
Furstner et al., "Ruthenium Carbene Complexes with N,N'-Bis(mesityl)imidazol-2-ylidene Ligands: RCM Catalysts of Extended Scope", J. Org. Chem., 2000, vol. 65, Issue 7, pp. 2204-2207.
Grant No. DE-FG36-04GO14016, "Platform Chemicals from an Oilseed Biorefinery," awarded by the Department of Energy, Final Technical Report, Nov. 30, 2006.

(Continued)

*Primary Examiner* — Rebecca Anderson
*Assistant Examiner* — Samantha L Shterengarts

(57) ABSTRACT

This invention relates to a catalyst compound comprising a combination of a cyclic alkyl amino carbene ligand and a benzylidene both attached to a Group 8 metal, preferably ruthenium atom.
This invention also relates to a process to make linear alpha-olefins comprising contacting a feed material and an optional alkene (such as ethylene) with the catalyst described above, wherein the feed material is a triacylglyceride, fatty acid, fatty acid alkyl ester, and/or fatty acid ester, typically derived from seed oil (e.g., biodiesel).

32 Claims, No Drawings

OTHER PUBLICATIONS

Hermann et al., "*Heterocyclic Carbenes: A High-Yielding Synthesis of Novel, Functionalized N-Heterocyclic Carbenes in Liquid Ammonia*", Chemistry, A European Journal, 1996, vol. 2, No. 12, pp. 1627-1636.

Hoveyda et al., "*A Recyclable Ru-Based Metathesis Catalyst*", Journal of American Chemical Society, 1999, vol. 121, pp. 791-799.

Kingsbury et al., "*A Recyclable Ru-Based Metathesis Catalyst*", J. Am. Chem. Soc., 1999, vol. 121, pp. 791-799.

Jazzar et al., "*A New Synthetic Method for the Preparation of Protonated-NHCs and Related Compounds*", Journal of Organometallic Chemistry, 2006, vol. 691, No. 14, pp. 3201-3205.

Jazzar et al., "*Intramolecular "Hydroiminiumation" of Alkenes: Application to the Synthesis of Conjugate Acids of Cyclic Alkyl Amino Carbenes (CAACs)*", Angewandte Chemie, International Edition, 2007, vol. 46, No. 16, pp. 2899-2902.

Lavallo et al., "*A Rigid Cyclic (Alkyl)amino)carbine) Ligand Leads to Isolation of Low-Coordinate Transition-Metal Complexes*", Angew. Chem. Int. Ed., 2005, vol. 44, No. 44, pp. 7236-7239.

Lavallo et al., "*Isolation of Cyclopropenylidene-Lithium Adducts: The Weiss-Yoshida Reagent*", Angewandte Chemie, International Edition, 2006, vol. 45, No. 40, pp. 6652-6655.

Lavallo et al., "*Stable Cyclic (Alkyl)(Amino)Carbenes as Rigid or Flexible, Bulky, Electron-Rich Ligands for Transition-Metal Catalysts: A quaternary Carbon Atom Makes the Difference*", Angew. Chem. Int. Ed., 2005, vol. 44, No. 35, pp. 5705-5709.

Rybak et al., "*Metathesis a Versatile Tool in Olechemistry*", Eur. J. Lipid Sci. Technol, Weinheim, 2008, vol. 110, pp. 797-804.

Scholl et al., "*Synthesis and Activity of A new Generation of Ruthenium-Based Olefin Metathesis Catalysts Coordinated with 1,3-Diesityl-4, 5-Dihydroimidazol-2-ylidene Ligands*" Org. Letters, 1999, vol. 1, pp. 953-956.

Schumann et al., "*Metallocenes of the Alkaline Earth Metals and Their Carbene Complexes*", Journal of Organometallic Chemistry, 2001, vol. 617-618, pp. 588-600.

Sigal et al., "*Are Disilacyclopropylidenes and Their Carbenoids Good Precursors for the Unknown 1, 3-Disilaallenes?*", Journal of Organometallic Chemistry, 2001, vol. 636, No. 1-2, pp. 148-156.

Stasch et al., "*Synthesis and Characterization of Alkynyl Complexes of Groups 1 and 2*", Chemistry, An Asian Journal, 2009, vol. 4, No. 9, pp. 1451-1457.

Tamm et al., "*Pentacarbonylchromium(0) and-tungsten(0) Complexes with the Bis(Diisopropylamino) Cyclopropenylidene Ligand*", Journal of Organometallic Chemistry, 1995, vol. 501, No. 1, pp. 309-313.

Vehlow et al., "*Ruthenium Metathesis Catalysts with Saturated Unsymmetrical N-Heterocyclic Carbene Ligands*", Organometallics, 2006, vol. 25, No. 1, pp. 25-28.

Allen et al., "*Well-Defined Silica-Supported Olefin Metathesis Catalysts*", Organic Letters, 2009, vol. 11, No. 6, pp. 1261-1264.

Blum et al., "*Synthesis of N-Heterocyclic Carbene-Containing Metal Complexes from 2-(Pentafluorophenyl)Imidazolidines*", Organometallics, 2007, vol. 26, No. 8, pp. 2122-2124.

Chung et al., "*Olefin Metathesis Catalyst: Stabilization Effect of Backbone Substitutions of N-Heterocyclic Carbene*", Organic Letters, 2008, vol. 10, No. 13, pp. 2693-2696.

Dinger et al., "*Adamantyl-Substituted N-Heterocyclic Carbene Ligands in Second-Generation Grubbs-Type Metathesis Catalysts*", Organometallics, 2003, vol. 22, No. 25, pp. 5291-5296.

Hermann et al., "*N-Heterocyclic Carbenes[+]: Generation under Mild Conditions and Formation of Groups 8-10 Transition Metal Complexes Relevant to Catalysts*", Chemistry, A European Journal, 1996, vol. 2, No. 7, pp. 772-780.

Ledoux et al., "*Comparative Investigation of Hoveyda-Grubbs Catalysts Bearing Modified N-Heterocyclic Carbene Ligands*", Advanced Synthesis & Catalysis, 2007, vol. 349, No. 10, pp. 1692-1700.

Ledoux et al., "*N-N'-Dialkyl- and N-Alkyl-N-Mesityl-Substituted N-Heterocyclic Carbenes as Ligands in Grubbs Catalysts*", Chemistry, A European Journal, 2006, vol. 12, No. 17, pp. 4654-4661.

Leuthaußer et al., "*π-Face Donor Properties of N-Heterocyclic Carbenes in Grubbs II Complexes*", Chemistry, A European Journal, 2008, vol. 14, No. 18, pp. 5465-5481.

Lichtenheldt et al., "*Alternating Ring-Opening Metathesis Copolymerization by Grubbs-Type Initiators with Unsymmetrical N-Heterocyclic Carbenes*", Chemistry, A European Journal, 2009, vol. 15, No. 37, pp. 9451-9457.

Santhosh Kumar et al., "*Factors Relevant for the Regioselective Cyclopolymerization of 1,6-Heptadiynes, N,N-Dipropargylamines, N,N-Dipropargylammonium Salts, and Dipropargyl Ethers by RuIV-Alklidene-Based Metathesis Initiators*", Journal of the American Chemical Society, 2009, vol. 131, No. 1, pp. 387-395.

Sulkier et al., "*π-Face Donor Properties of N-Heterocyclic Carbenes*", Chemical Communications, 2005, No. 43, pp. 5417-5419.

Tiede et al., "*Highly Active Chiral Ruthenium-based Metathesis Catalysts Through a Monosubstitution in the N-Heterocyclic Carbene*", Angewandte Chemie, International Edition, 2010, vol. 49, No. 23, pp. 3972-3975.

Vehlow et al., "*Alternating Copolymerizations Using a Grubbs-Type Initiator with an Unsymmetrical, Chiral N-Heterocyclic Carbene Ligand*", Angewandte Chemie, International Edition, 2008, vol. 47, No. 14, pp. 2615-2618.

Vehlow et al., "*Deactivation of Ruthenium Olefin Metathesis Catalysts Through Intromolecular Carbene-Arene Bond Formation*", Angewandte Chemie, International Edition, 2007, vol. 46, No. 42, pp. 8082-8085.

Vougioukalakis et al., "*Ruthenium-Based Olefin Metathesis Catalysts Coordinated with Unsymmetrical N-Heterocyclic Carbene Ligands: Synthesis, Structure, and Catalytic Activity*", Chemistry, A European Journal, 2008, vol. 14, No. 25, pp. 7545-7556.

Vougioukalakis et al., "*Ruthenium Olefin Metathesis Catalysts Bearing an N-Fluorophenyl-N-MesitylSubstituted Unsymmetrical N-Heterocyclic Carbene*", Organometallics, 2007, vol. 26, No. 9, pp. 2469-2472.

Xu et al., "*Development of Building Blocks for the Synthesis of N-Heterocyclic Carbene Ligands*", Organic Letters, 2005, vol. 7, No. 21, pp. 4605-4608.

Arnold et al., "*Asymmetric Lithium(I) and Copper (II) Alkoxy-N-Heterocyclic Carbene Complexes; Crystallographic Charaterisation and Lewis Acid Catalysis*", Chemical Communications, 2004, pp. 1612-1613.

Arnold et al., "*Anionic Amido N-Heterocyclic Carbenes; Synthesis of Covalently Tethered Lanthanide-Carbene Complexes*", Angewandte Chemie International Edition, 2003, vol. 42, pp. 5981-5984.

De Fremont et al., "*Cationic NHC-Gold(I) Complexes: Synthesis, Isolation and Catalytic Activity*", Journal of Organometallic Chemistry, 2009, vol. 694, pp. 551-560.

Frankel et al., "*A Homopletic Carbene-Lithium Complex*", Angewandte Chemie International Edition, 2001, vol. 40, No. 10, pp. 1907-1910.

Hahn et al., "*Heterocyclic Carbenes: Synthesis and Coordination Chemistry*", Angewandte Chemie International Edition, 2008, vol. 47, pp. 3122-3172.

METATHESIS CATALYST AND PROCESS FOR USE THEREOF

PRIORITY CLAIM

This invention claims priority to and the benefit of U.S. Ser. No. 61/259,514, filed Nov. 9, 2009.

STATEMENT OF RELATED APPLICATIONS

The invention is related to patent application U.S. Ser. No. 12/939,063, filed concurrently herewith and claiming priority to U.S. Ser. No. 61/259,521, filed Nov. 9, 2009.

FIELD OF THE INVENTION

This invention relates to metathesis catalyst compounds and processes for the use thereof.

BACKGROUND OF THE INVENTION

The cross-metathesis of ethylene and internal olefin to produce alpha-olefins is generally referred to as ethenolysis. Olefins Conversion Technology™, based upon the Phillips Triolefin Process, is an example of an ethenolysis reaction converting ethylene and 2-butene into propylene. These processes uses heterogeneous catalysts, such as tungsten and rhenium oxides, which have not proven effective for internal olefins containing functional groups such as cis-methyl oleate, a fatty acid methyl ester.

Methods for the production of polyalpha-olefins are typically multi-step processes that often create unwanted by-products and waste of reactants and energy. Full range linear alpha-olefins plants are petroleum-based, are inefficient and result in mixtures of oligomerization products that typically yield Schulz-Flory distributions producing large quantities of undesirable materials. In recent years there have been new technologies implemented to produce "on purpose" linear alpha-olefins such 1-hexene and 1-octene through chromium-based selective ethylene trimerization or tetramerization catalysts. Alternatively, 1-octene has been produced via the telomerization of butadiene and methanol. Similar strategies are not currently available for the production of 1-decene.

1-Decene is a co-product in the cross-metathesis of ethylene and methyl oleate. Alkyl oleates are fatty acid esters that can be major components in biodiesel produced by the transesterification of alcohol and vegetable oils. Vegetable oils containing at least one site of unsaturation include canola, soybean, palm, peanut, mustard, sunflower, tung, tall, perilla, grapeseed, rapeseed, linseed, safflower, pumpkin corn and many other oils extracted from plant seeds. Alkyl erucates similarly are fatty acid esters that can be major components in biodiesel. Useful biodiesel compositions are those which typically have high concentrations of oleate and erucate esters. These fatty acid esters preferably have one site of unsaturation such that cross-metathesis with ethylene yields 1-decene as a co-product.

Biodiesel is a fuel prepared from renewable sources, such as plant oils or animal fats. To produce biodiesel, triacylglycerides ("TAG"), the major compound in plant oils and animal fats, are converted to fatty acid alkyl esters ("FAAE," i.e., biodiesel) and glycerol via reaction with an alcohol in the presence of a base, acid, or enzyme catalyst. Biodiesel fuel can be used in diesel engines, either alone or in a blend with petroleum-based diesel, or can be further modified to produce other chemical products.

Cross-metathesis catalysts reported thus far for the ethenolysis of methyl oleate are typically ruthenium-based catalysts bearing phosphine or carbene ligands. Dow researchers in 2004 achieved catalysts turnovers of approximately 15,000 using the $1^{st}$ generation Grubb's catalyst, bis(tricyclohexylphosphine)benzylidene ruthenium(IV) dichloride, (Organometallics 2004, 23, 2027). Researchers at Materia, Inc. have reported turnover numbers up to 35,000 using a ruthenium catalyst containing a cyclic alkyl amino carbene ligand, (WO 2008/010961). These turnovers were obtained with a catalyst reportedly too expensive for industrial consideration due to high costs associated with the catalysts being derived from a low yielding synthesis (See Final Technical Report entitled "Platform Chemicals from an Oilseed Biorefinery" grant number DE-FG36-04G014016 awarded by the Department of Energy). In order to obtain an economically viable process for 1-decene production via the cross-metathesis of ethylene and biodiesel or vegetable oils, higher activity catalysts must be discovered. Thus there is a need for higher activity processes that produce desired products and co-products in commercially desirable ratios.

Likewise, there is a need to develop a means to provide linear alpha-olefins (particularly high yields of linear alpha-olefins) by metathesis reactions, particularly reactions with good conversion, preferably under mild reaction conditions is a minimal number of steps. The instant invention's metathesis catalyst provides both a commercially economical and an "atom-economical" route to linear alpha-olefins.

Specifically, the instant inventors have found that the combination of a cyclic alkyl amino carbene ligand attached to ruthenium with a chelating benzylidene ligand containing an electron withdrawing group yielded a catalyst that is both highly active and very selective towards the ethenolysis of methyl oleate yielding 1-decene and methyl-9-decenoate.

SUMMARY OF THE INVENTION

This invention relates to a process comprising contacting a seed oil or derivative thereof (and optional alkene) with an olefin metathesis catalyst under conditions which yield an alpha-olefin.

This invention relates to a process comprising contacting a triacylglyceride or derivative thereof (and optional alkene) with an olefin metathesis catalyst under conditions which yield an alpha-olefin.

The novel process of this invention employs a novel catalyst comprising the combination of a cyclic alkyl amino carbene ligand and a benzylidene ligand containing an electron withdrawing substituent on the aromatic ring of the benzylidene both attached to a Group 8 metal, preferably ruthenium atom.

This invention further relates to a metathesis catalyst is represented by the formula:

Formula (I)

[Chemical structure showing a ruthenium complex with substituents $R^1$ through $R^{13}$, groups labeled M, X, $X^1$, L, G, H, C, N, and an $SO_2N-R_2$ group]

where:
M is a Group 8 metal;
X and $X^1$ are, independently, any anionic ligand, or X and $X^1$ may be joined to form a dianionic group and may form single ring of up to 30 non-hydrogen atoms or a multinuclear ring system of up to 30 non-hydrogen atoms;

L is N, O, P, or S;

R is hydrogen or a $C_1$ to $C_{30}$ hydrocarbyl or substituted hydrocarbyl;

$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;

each $R^9$ and $R^{13}$ are, independently, hydrogen or a $C_1$ to $C_{30}$ hydrocarbyl or substituted hydrocarbyl;

$R^{10}$, $R^{11}$, $R^{12}$ are, independently, hydrogen or a $C_1$ to $C_{30}$ hydrocarbyl or substituted hydrocarbyl;

each G, is, independently, hydrogen, halogen or $C_1$ to $C_{30}$ substituted or unsubstituted hydrocarbyl, where any two adjacent R groups may form a single ring of up to 8 non-hydrogen atoms or a multinuclear ring system of up to 30 non-hydrogen atoms.

DETAILED DESCRIPTION

This invention relates to a process comprising contacting a seed oil or derivative thereof (and optional alkene) with an olefin metathesis catalyst under conditions which yield an alpha-olefin. Typically the seed oil is esterified or transesterified with an alcohol prior to contacting with the olefin metathesis catalyst.

This invention relates to a process comprising contacting a triacylglyceride or a derivative thereof with an optional alkene (such as ethylene) and an olefin metathesis catalyst under conditions which yield an alpha-olefin, typically yielding a linear alpha-olefin (such as 1-decene, 1-heptene, and/or 1-butene) and an ester or acid functionalized olefin.

This invention further relates to a process for producing alpha-olefins (preferably linear alpha-olefins) comprising contacting a triacylglyceride with an alcohol (such as methanol) to produce a fatty acid alkyl ester and thereafter contacting the fatty acid alkyl ester with an olefin metathesis catalyst (and optional alkene, such as ethylene) under conditions which yield an alpha-olefin (preferably a linear alpha-olefin, preferably 1-decene, 1-heptene, and/or 1-butene) and an ester or acid functionalized olefin.

This invention further relates to a process for producing alpha-olefins (preferably linear alpha-olefins) comprising contacting a triacylglyceride with water and or an alkaline reactant (such as sodium hydroxide) to produce a fatty acid and thereafter contacting the fatty acid with an olefin metathesis catalyst (and optional alkene, such as ethylene) under conditions which yield an alpha-olefin (preferably a linear alpha-olefin, preferably 1-decene, 1-heptene, and/or 1-butene) and an ester or acid functionalized olefin.

This invention further relates to contacting unsaturated fatty acid with an alkene (such as ethylene) in the presence of an olefin metathesis catalyst under conditions which yield an alpha-olefin (preferably a linear alpha-olefin, preferably 1-decene, 1-heptene, and/or 1-butene) and an ester or acid functionalized olefin.

This invention further relates to contacting an unsaturated fatty acid ester with a alkene (such as ethylene) in the presence of an olefin metathesis catalyst under conditions which yield an alpha-olefin (preferably a linear alpha-olefin, preferably 1-decene, 1-heptene, and/or 1-butene) and an ester or acid functionalized olefin.

This invention further relates to contacting an unsaturated fatty acid alkyl ester with a alkene (such as ethylene) in the presence of an olefin metathesis catalyst under conditions which yield an alpha-olefin (preferably a linear alpha-olefin, preferably 1-decene, 1-heptene, and/or 1-butene) and an ester or acid functionalized olefin.

This invention also relates to a process to produce alpha olefin (preferably linear alpha olefin, preferably 1-decene, 1-heptene and or 1-butene) comprising contacting a metathesis catalyst with an alkene (preferably ethylene), and one or more fatty acid esters (preferably fatty acid methyl esters, preferably methyl oleate).

In a preferred embodiment, this relates to a process to produce alpha olefin (preferably linear alpha olefin, preferably 1-decene, 1-heptene and or 1-butene) comprising contacting a metathesis catalyst with an alkene (preferably ethylene), and one or more fatty acid esters (preferably fatty acid methyl esters, preferably methyl oleate) derived from biodiesel.

In a preferred embodiment, the olefin metathesis catalysts described herein may be combined directly with triacylglycerides, biodiesel, fatty acids, fatty acid esters and/or fatty acid alkyl esters to produce alpha-olefins, preferably linear alpha olefins, preferably $C_4$ to $C_{24}$ alpha-olefins, preferably linear alpha-olefins, such as 1-decene, 1-heptene and or 1-butene.

In a preferred embodiment, a mixture of one or more triacylglyceride, biodiesel, fatty acids, fatty acid esters and/or fatty acid alkyl esters are used to produce alpha-olefins, preferably linear alpha olefins, preferably $C_4$ to $C_{24}$ alpha-olefins, preferably $C_4$ to $C_{24}$ linear alpha-olefins. In a preferred embodiment a mixture of alpha olefins, preferably linear alpha olefins, preferably 1-decene, 1-heptene and or 1-butene are produced.

Process

In a preferred embodiment, the metathesis catalysts described herein may be combined directly with seed oils, triacylglyceride, biodiesel, fatty acids, fatty acid esters and/or fatty acid alkyl esters ("feed materials") to produce alpha-olefins, preferably linear alpha olefins, preferably $C_4$ to $C_{24}$ alpha-olefins, preferably $C_4$ to $C_{24}$ linear alpha-olefins, such as preferably 1-decene, 1-heptene and or 1-butene.

Typically, the molar ratio of alkene to unsaturated feed material (such as unsaturated fatty acid or fatty acid ester) is greater than about 0.8/1.0, preferably, greater than about 0.9/1.0. Typically, the molar ratio of alkene to feed material (such as unsaturated fatty acid or fatty acid ester) is less than about 3.0/1.0, preferably, less than about 2.0/1.0. Depending upon the specific reagents, other molar ratios may also be suitable. With ethylene, for example, a significantly higher molar ratio can be used, because the self-metathesis of ethylene produces only ethylene again; no undesirable co-product olefins are formed. Accordingly, the molar ratio of ethylene to feed material (such as unsaturated fatty acid or fatty acid ester) may range from greater than about 0.8/1 to typically less than about 20/1.

The quantity of metathesis catalyst that is employed in the process of this invention is any quantity that provides for an operable metathesis reaction. Preferably, the ratio of moles of feed material (preferably fatty acid ester and or fatty acid alkyl ester) to moles of metathesis catalyst is typically greater than about 10:1, preferably, greater than about 100:1, preferably greater than about 1000:1, preferably greater than about 10,000:1, preferably greater than about 25,000:1, preferably greater than about 50,000:1, preferably greater than about 100,000:1. Alternately, the molar ratio of feed material (preferably fatty acid ester and or fatty acid alkyl ester) to metathesis catalyst is typically less than about 10,000,000:1, preferably, less than about 1,000,000:1, and more preferably, less than about 500,000:1.

The contacting time of the reagents and catalyst in a batch reactor can be any duration, provided that the desired olefin metathesis products are obtained. Generally, the contacting time in a reactor is greater than about 5 minutes, and preferably, greater than about 10 minutes. Generally, the contacting time in a reactor is less than about 25 hours, preferably, less than about 15 hours, and more preferably, less than about 10 hours.

In a preferred embodiment, the reactants (for example, metathesis catalyst; feed materials; optional alkene, optional alcohol, optional water, etc) are combined in a reaction vessel at a temperature of 20 to 200° C. (preferably 30 to 100° C., preferably 40 to 60° C.) and an alkene (such as ethylene) pressure of 0.1 to 1000 psi (preferably 20 to 400 psi, preferably 50 to 250 psi), if the alkene is present, for a residence time of 0.5 seconds to 48 hours (preferably 0.25 to 5 hours, preferably 30 minutes to 2 hours).

In a preferred embodiment, from about 0.005 nmoles to about 500 nmoles, preferably from about 0.1 to about 250 nmoles, and most preferably from about 1 to about 50 nmoles of the metathesis catalyst are charged to the reactor per 3 mmoles of feed material (such as TAGs, biodiesel, fatty acids, fatty acid esters and/or fatty acid alkyl esters or mixtures thereof, preferably fatty acid esters) charged.

In a preferred embodiment, the alkane and an unsaturated fatty acid ester or unsaturated fatty acid are co-metathesized to form first and second product olefins, preferably, a reduced chain first product alpha-olefin and a second product reduced chain terminal ester or acid-functionalized alpha-olefin. As a preferred example, the metathesis of methyloleate with ethylene will yield co-metathesis products of 1-decene and methyl-9-decenoate. Both products are alpha-olefins; the decenoate also terminates in an ester moiety at the opposite end of the chain from the carbon-carbon double bond. In addition to the desired products, the methyloleate may self-metathesize to produce small amounts of 9-octadecene, a less desirable product, and dimethyloctadec-9-enoate, $CH_3O(O)C(CH_2)_7CH=CH(CH_2)_7C(O)OCH_3$, a second less desirable product.

In the process of this invention, the conversion of feed material (preferably fatty acid ester and or fatty acid alkyl ester) can vary widely depending upon the specific reagent olefins, the specific catalyst, and specific process conditions employed. For the purpose of this invention, "conversion" is defined as the mole percentage of feed material that is converted or reacted to products. Typically, the conversion of feed material (preferably fatty acid ester and or fatty acid alkyl ester) is greater than about 50 mole percent, preferably, greater than about 60 mole percent, and more preferably, greater than about 70 mole percent.

In the process of this invention, the yields of first product olefin and ester or acid-functionalized second product olefin can also vary depending upon the specific reagent olefins, catalyst, and process conditions employed. For the purposes of this invention "yield" will be defined as the mole percentage of product olefin formed relative to the initial moles of feed material (such as fatty acid ester and or fatty acid alkyl ester) in the feed. Typically, the yield of alpha-olefin will be greater than about 35 mole percent, preferably, greater than about 50 mole percent. Typically, the yield of ester or acid-functionalized alpha-olefin will be greater than about 35 mole percent, preferably, greater than about 50 mole percent.

In a preferred embodiment, the process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 volume % or more.) Alternately no solvent or diluent is present or added in the reaction medium, (except for the small amounts used as the carrier for the catalyst or other additives, or amounts typically found with the reactants; e.g., propane in propylene).

Suitable diluents/solvents for the process include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof such as can be found commercially (Isopar™); perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable diluents/solvents also include aromatic hydrocarbons, such as toluene or xylenes, and chlorinated solvents, such as dichloromethane. In a preferred embodiment, the feed concentration for the process is 60 volume % solvent or less, preferably 40 volume % or less, preferably 20 volume % or less.

The process may be batch, semi-batch or continuous. As used herein, the term continuous means a system that operates without interruption or cessation. For example, a continuous process to produce a polymer would be one where the reactants are continually introduced into one or more reactors and polymer product is continually withdrawn.

Useful reaction vessels include reactors (including continuous stirred tank reactors, batch reactors, reactive extruder, pipe or pump.

If the process is conducted in a continuous flow reactor, then the weight hourly space velocity, given in units of grams feed material (preferably fatty acid ester and or fatty acid alkyl ester) per gram catalyst per hour ($h^{-1}$), will determine the relative quantities of feed material to catalyst employed, as well as the residence time in the reactor of the unsaturated starting compound. In a flow reactor, the weight hourly space velocity of the unsaturated feed material (preferably fatty acid ester and or fatty acid alkyl ester) is typically greater than about 0.04 g feed material (preferably fatty acid ester and or fatty acid alkyl ester) per g catalyst per hour ($h^{-1}$), and preferably, greater than about 0.1 $h^{-1}$. In a flow reactor, the weight hourly space velocity of the feed material (preferably fatty acid ester and or fatty acid alkyl ester) is typically less than about 100 $h^{-1}$, and preferably, less than about 20 $h^{-1}$.

In a preferred embodiment, the productivity of the process is at least 200 g of linear alpha-olefin (such as decene-1) per mmol of catalyst per hour, preferably at least 5000 g/mmol/hour, preferably at least 10,000 g/mmol/hr, preferably at least 300,000 g/mmol/hr.

In a preferred embodiment, the selectivity of the process is at least 20 wt % linear alpha-olefin, based upon the weight to the material exiting the reactor, preferably at least 25%, preferably at least 30%, preferably at least 35%.

In a preferred embodiment, the turnover number (TON), defined as the moles of alpha olefin formed per mol of catalyst, of the process is at least 10,000, preferably at least 50,000, preferably at least 100,000, preferably at least 1,000,000.

In a preferred embodiment, the yield (when converting unsaturated fatty acids, unsaturated fatty acid esters, unsaturated fatty acid alkyl esters or mixtures thereof), defined as the moles of alpha olefin formed per mol of unsaturated fatty acids, unsaturated fatty acid esters, unsaturated fatty acid alkyl esters or mixtures thereof introduced into the reactor, is 30% or more, preferably 40% or more, preferably 45% or more, preferably 50% or more, preferably 55% or more, preferably 60% or more.

In a preferred embodiment, the yield for reactions (when converting TAGs as represented in the formula below), is defined as the moles of alpha olefin formed divided by (the moles of unsaturated $R^a$+moles of unsaturated $R^b$+moles of unsaturated $R^c$) introduced into the reactor is 30% or more, preferably 40% or more, preferably 45% or more, preferably 50% or more, preferably 55% or more, preferably 60% or more.

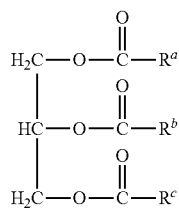

where $R^a$, $R^b$ and $R^c$ each, independently, represent a saturated or unsaturated hydrocarbon chain (preferably $R^a$, $R^b$ and $R^c$ each, independently, are a $C_{12}$ to $C_{28}$ alkyl or alkene, preferably $C_{16}$ to $C_{22}$ alkyl or alkene).

Alkenes

Besides the feed materials, the metathesis process of this invention may require a an alkene as a reactant. The term "alkene" shall imply an organic compound containing at least one carbon-carbon double bond and typically having less than about 10 carbon atoms. The alkene may have one carbon-carbon unsaturated bond, or alternatively, two or more carbon-carbon unsaturated bonds. Since the metathesis reaction can occur at any double bond, alkenes having more than one double bond will produce more metathesis products. Accordingly, in some embodiments, it is preferred to employ an alkene having only one carbon-carbon double bond. The double bond may be, without limitation, a terminal double bond or an internal double bond. The alkene may also be substituted at any position along the carbon chain with one or more substituents, provided that the one or more substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities. Non-limiting examples of suitable alkenes include ethylene, propylene, butene, butadiene, pentene, hexene, the various isomers thereof, as well as higher homologues thereof. Preferably, the alkene is a $C_{2-8}$ alkene. More preferably, the alkene is a $C_{2-6}$ alkene, even more preferably, a $C_{2-4}$ alkene, and most preferably, ethylene.

Useful alkenes include those represented by the formula: $R^*$—HC=CH—$R^*$, wherein each $R^*$ is independently, hydrogen or a $C_1$ to $C_{20}$ hydrocarbyl, preferably hydrogen or a $C_1$ to $C_6$ hydrocarbyl, preferably hydrogen, methyl, ethyl, propyl or butyl, more preferably $R^*$ is hydrogen. In a preferred embodiment, both $R^*$ are the same, preferably both $R^*$ are hydrogen. Ethylene, propylene, butene, pentene, hexene, octene and nonene (preferably ethylene) are alkenes useful herein.

For purposes of this invention and the claims thereto, the term lower olefin means an alkene represented by the formula: $R^*$—HC=CH—$R^*$, wherein each $R^*$ is independently, hydrogen or a $C_1$ to $C_6$ hydrocarbyl, preferably hydrogen or a $C_1$ to $C_3$ hydrocarbyl, preferably hydrogen, methyl, ethyl, propyl or butyl, more preferably $R^*$ is hydrogen. In a preferred embodiment, both $R^*$ are the same, preferably both $R^*$ are hydrogen. Ethylene, propylene, butene, pentene, hexene, and octene (preferably ethylene) are lower olefins useful herein.

Triacylglycerides

Triacylglycerides (TAGs), also called triglycerides, are a naturally occurring ester of three fatty acids and glycerol that is the chief constituent of natural fats and oils. The three fatty acids can be all different, all the same, or only two the same, they can be saturated or unsaturated fatty acids, and the saturated fatty acids may have one or multiple unsaturations. Chain lengths of the fatty acids in naturally occurring triacylglycerides can be of varying lengths but 16, 18 and 20 carbons are the most common. Natural fatty acids found in plants and animals are typically composed only of even numbers of carbon atoms due to the way they are bio-synthesized. Most natural fats contain a complex mixture of individual triglycerides and because of this, they melt over a broad range of temperatures.

Biodiesel is a mono-alkyl ester derived from the processing of vegetable oils and alcohols. The processing is typically carried out by an esterification reaction mechanism, and typically is performed in an excess of alcohol to maximize conversion. Esterification can refer to direct esterification, such as between a free fatty acid and an alcohol, as well as transesterification, such as between an ester and an alcohol. While vegetable oil and alcohols are commonly employed as reactants in esterification reactions, a fatty acid source such as free fatty acids, soaps, esters, glycerides (mono-, di- tri-), phospholipids, lysophospholipids, or amides and a monohydric alcohol source, such as an alcohol or an ester, can be esterified. In addition, various combinations of these reagents can be employed in an esterification reaction.

Vegetable oils include triglycerides and neutral fats, such as triacylglyderides, the main energy storage form of fat in animals and plants. These typically have the chemical structure:

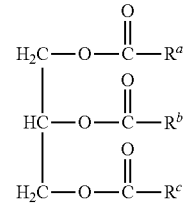

where $R^a$, $R^b$ and $R^c$ each, independently, represent a saturated or non-saturated hydrocarbon chain (preferably $R^a$, $R^b$ and $R^c$ each, independently, are a $C_{12}$ to $C_{28}$ alkyl or alkene, preferably $C_{16}$ to $C_{22}$ alkyl or alkene). Different vegetable oils have different fatty acid profiles, with the same or different fatty acids occurring on a single glycerol. For example, an oil can have linoleic, oleic, and stearic acids attached to the same glycerol, with each of $R^a$, $R^b$ and $R^c$ representing one of these three fatty acids. In another example, there can be two oleic acids and one stearic acid attached to the same glycerol, each of $R^a$, $R^b$ and $R^c$ representing one of these fatty acids. A particularly useful triglyceride consists of three fatty acids (e.g., saturated fatty acids of general structure of $CH_3(CH_2)_n$COOH, wherein n is typically an integer of from 4 to 28 or higher) attached to a glycerol ($C_3H_5(OH)_3$) backbone by ester linkages. In the esterification process, vegetable oils and short chain alcohols are reacted to form mono-alkyl esters of the fatty acid and glycerol (also referred to as glycerin). When the alcohol used is methanol ($CH_3OH$), a methyl ester is created with the general form $CH_3(CH_2)_nCOOCH_3$ for saturated fatty acids. Typically, but not always, the length of the carbon backbone chain is from 12 to 24 carbon atoms.

The esterification process can be catalyzed or non-catalyzed. Catalyzed processes are categorized into chemical and enzyme based processes. Chemical catalytic methods can employ acid and/or base catalyst mechanisms. The catalysts can be homogeneous and/or heterogeneous catalysts. Homogeneous catalysts are typically liquid phase mixtures, whereas heterogeneous catalysts are solid phase catalysts mixed with the liquid phase reactants, oils and alcohols.

The fatty acid rich material useful in the processes described herein can be derived from plant, animal, microbial, or other sources (feed oil). Preferred feed oils include vegetable oils such as corn, soy, rapeseed, canola, sunflower, palm and other oils that are readily available; however, any vegetable oil or animal fat can be employed. Raw or unrefined oil can be used in certain embodiments; however, filtered and refined oils are typically preferred. Use of degummed and filtered feedstock minimizes the potential for emulsification and blockage in the reactors. Feedstock with high water content can be dried before basic catalyst processing. Feedstock with high free fatty acid content can be passed through an esterification process to reduce the free fatty acid content before the process of esterification to convert fatty acid glycerides to monoalkyl esters. The reduction of free fatty acids and the conversion of fatty acid glycerides can also in the same processing step. Feedstock containing other organic compounds (such as hexane, heptane, isohexane, etc.) can typically be processed without significant modifications to the reactor. Other materials containing fatty acid glycerides or other fatty acid esters can also be employed, including phospholipids, lysophospholipids, and fatty acid wax esters. The fatty acid rich material useful in the processes described herein typically includes a mixture of fatty acids. For example, the fatty acid profiles of several potential feedstocks are shown in Table 1. The feed oil can also include a mixture of fatty acid glycerides from different sources. The free fatty acid content of useful vegetable oils is preferably about 0.1 wt % or less when employed in a basic homogeneous catalyst esterification reaction. Higher levels can be utilized as well, and levels up to about 3 wt %, or even as high as 15 wt % or more can typically be tolerated.

TABLE 1

Fatty Acid Profile of Several Typical Feed Oils

| Fatty Acid | Palm Oil | Soy Oil | Hi Oleic Rapeseed | Yellow Grease |
|---|---|---|---|---|
|  | 0 wt % | 0 wt % | 0 wt % | 0 wt % |
| C6:0 | 0 wt % | 0 wt % | 0 wt % | 0 wt % |
| C8:0 | 0 wt % | 0 wt % | 0 wt % | 0 wt % |
| C10:0 | 0 wt % | 0 wt % | 0 wt % | 0 wt % |
| C12:0 | 0 wt % | 0 wt % | 0 wt % | 0 wt % |
| C14:0 | 1 wt % | 0 wt % | 0 wt % | 2 wt % |
| C16:0 | 44 wt % | 7 wt % | 4 wt % | 23 wt % |
| C18:0 | 5 wt % | 5 wt % | 1 wt % | 13 wt % |
| C18:1 | 39 wt % | 28 wt % | 60 wt % | 44 wt % |
| C18:2 | 10 wt % | 53 wt % | 21 wt % | 7 wt % |
| C18:3 | 0 wt % | 0 wt % | 13 wt % | 1 wt % |
| C20:0 | 0 wt % | 0 wt % | 0 wt % | 0 wt % |
| C22:1 | 0 wt % | 0 wt % | 0 wt % | 0 wt % |
| Misc. | 1 wt % | 8 wt % | 0 wt % | 9 wt % |
| Total | 100 wt % | 100 wt % | 100 wt % | 100 wt % |

Alcohol (also Referred to as Alkanols)

The alcohol used herein can be any monohydric, dihydric, or polyhydric alcohol that is capable of condensing with the feed material (such as the unsaturated fatty acid) to form the corresponding unsaturated ester (such as the fatty acid ester). Typically, the alcohol contains at least one carbon atom. Typically, the alcohol contains less than about 20 carbon atoms, preferably, less than about 12 carbon atoms, and more preferably, less than about 8 carbon atoms. The carbon atoms may be arranged in a straight-chain or branched structure, and may be substituted with a variety of substituents, such as those previously disclosed hereinabove in connection with the fatty acid, including the aforementioned alkyl, cycloalkyl, monocyclic aromatic, arylalkyl, alkylaryl, hydroxyl, halogen, ether, ester, aldehyde and keto substituents. Preferably, the alcohol is a straight-chain or branched $C_{1-12}$ alkanol. A preferred alcohol is the trihydric alcohol glycerol, the fatty acid esters of which are known as "glycerides." Other preferred alcohols include methanol and ethanol.

Preferably, the alcohol employed in the esterification and/or transesterification reactions is preferably a low molecular weight monohydric alcohol such as methanol, ethanol, 1-propanol, 2-propanol, 1-butanol, 2-butanol, or t-butanol. The alcohol is preferably anhydrous; however, a small amount of water in the alcohol may be present (e.g., less than about 2 wt %, preferably less than about 1 wt %, and most preferably less than about 0.5 wt %; however in certain embodiments higher amounts can be tolerated). Acid esterification reactions are more tolerant of the presence of small amounts of water in the alcohol than are basic transesterification reactions. While specific monohydric alcohols are discussed herein with reference to certain embodiments and examples, the preferred embodiments are not limited to such specific monohydric alcohols. Other suitable monohydric alcohols can also be employed in the preferred embodiments.

Transesterification/Esterification Reactions

The conversion of TAGs to fatty acid alkyl esters ("FAAE") through transesterification of the TAG typically involves forming a reactant stream, which includes TAG (e.g., at least about 75 wt %), alkanol (e.g., about 5 to 20 wt %), a transesterification catalyst (e.g., about 0.05 to 1 wt %), and optionally, glycerol (typically up to about 10 wt %). Suitable alkanols may include $C_1$-$C_6$ alkanols and commonly may include methanol, ethanol, or mixtures thereof. Suitable transesterification catalysts may include alkali metal alkoxides having from 1 to 6 carbon atoms and commonly may include alkali metal methoxide, such as sodium methoxide and/or potassium methoxide. The basic catalyst is desirably selected such that the alkali metal alkoxide may suitably contain an alkoxide group which is the counterpart of the alkanol employed in the reaction stream (e.g., a combination of methanol and an alkali metal methoxide such as sodium methoxide and/or potassium methoxide). The reactant stream may suitably include about 0.05 to 0.3 wt % sodium methoxide, at least about 75 wt % triacylglyceride, about 1 to 7 wt % glycerol, and at least about 10 wt % methanol. In some embodiments, the reactant stream may desirably include about 0.05 to 0.25 wt % sodium methoxide, at least about 75 wt % triacylglyceride, about 2 to 5 wt % glycerol, and about 10 to 15 wt % methanol.

The rate and extent of reaction for esterification of the fatty acid glycerides or other fatty acid derivates with monohydric alcohol in the presence of a catalyst depends upon factors including but not limited to the concentration of the reagents, the concentration and type of catalyst, and the temperature and pressure conditions, and time of reaction. The reaction generally proceeds at temperatures above about 50° C., preferably at temperatures above 65° C.; however, the catalyst selected or the amount of catalyst employed can affect this temperature to some extent. Higher temperatures generally result in faster reaction rates. However, the use of very high temperatures, such as those in excess of about 300° C., or even those in excess of 250° C., can lead to increased generation of side products, which can be undesirable as their presence can increase downstream purification costs. Higher temperatures can be advantageously employed, however, e.g., in situations where the side products do not present an issue.

The reaction temperature can be achieved by preheating one or more of the feed materials or by heating a mixture of the feed materials. Heating can be achieved using apparatus known in the art e.g., heat exchangers, jacketed vessels, submerged coils, and the like. While specific temperatures and methods of obtaining the specific temperatures are discussed herein with reference to certain embodiments and examples, the preferred embodiments are not limited to such specific temperatures and methods of obtaining the specific temperatures. Other temperatures and methods of obtaining temperatures can also be employed in the preferred embodiments.

The amount of alcohol employed in the reaction is preferably in excess of the amount of fatty acid present on a molar basis. The fatty acid can be free or combined, such as to alcohol, glycol or glycerol, with up to three fatty acid moieties being attached to a glycerol. Additional amounts of alcohol above stoichiometric provide the advantage of assisting in driving the equilibrium of the reaction to produce more of the fatty acid ester product. However, greater excesses of alcohol can result in greater processing costs and larger capital investment for the larger volumes of reagents employed in the process, as well as greater energy costs associated with recovering, purifying, and recycling this excess alcohol. Accordingly, it is generally preferred to employ an amount of alcohol yielding a molar ratio of alcohol to fatty acid of from about 15:1 to about 1:1 (stoichiometric), and more preferably from about 4:1 to about 2:1; however, the process can operate over a much wider range of alcohol to fatty acid ratios, with non-reacted materials subjected to recycling or other processing steps. Generally, lower relative levels of alcohol to fatty acid result in decreased yield and higher relative levels of alcohol levels to fatty acid result in increased capital and operating expense. Some instances of operation at ratios of alcohol to fatty acid over a wider range include when first starting up the process or shutting down the process, when balancing the throughput of the reactor to other processing steps or other processing facilities, such as one that produces alcohol or utilizes a side stream, or when process upsets occur. When a molar ratio of 2:1 methanol to fatty acid is employed and a sodium hydroxide concentration of about 0.5 wt % of the total reaction mixture is employed, the ratio of sodium hydroxide to methanol is about 2 wt % entering the reactor and about 4 wt % at the exit because about half of the alcohol is consumed in the esterification reaction.

Similarly, higher amounts of catalyst generally result in faster reactions. However, higher amounts of catalyst can lead to higher downstream separation costs and a different profile of side reaction products. The amount of homogeneous catalyst is preferably from about 0.2 wt % to about 1.0 wt % of the reaction mixture when the catalyst is sodium hydroxide; at typical concentration of 0.5 wt % when a 2:1 molar ratio of methanol to fatty acid is used; however, in certain embodiments higher or lower amounts can be employed. The amount of catalyst employed can also vary depending upon the nature of the catalyst, feed materials, operating conditions, and other factors. Specifically, the temperature, pressure, free fatty acid content of the feed, and degree of mixing can change the amount of catalyst preferably employed. While specific catalyst amounts are discussed herein with reference to certain embodiments and examples, the preferred embodiments are not limited to such specific catalyst amounts. Other suitable catalyst amounts can also be employed in the preferred embodiments.

The esterification reaction can be performed batchwise, such as in a stirred tank, or it can be performed continuously, such as in a continuous stirred tank reactor (CSTR) or a plug flow reactor (PFR). When operated in continuous mode, a series of continuous reactors (including CSTRs, PFRs, or combinations thereof) can advantageously operate in series. Alternatively, batch reactors can be arranged in parallel and/or series.

When the reactor is operated in a continuous fashion, one or more of the feed materials is preferably metered into the process. Various techniques for metering can be employed (e.g., metering pumps, positive displacement pumps, control valves, flow meters, and the like). While specific types of reactors are discussed herein with reference to certain embodiments and examples, the preferred embodiments are not limited to such specific reactors. Other suitable types of reactors can also be employed in the preferred embodiments.

Fatty Acids and Fatty Acid Esters

Fatty acids are carboxylic acids with a saturated or unsaturated aliphatic tails that are found naturally in many different fats and oils. Any unsaturated fatty acid can be suitably employed in the process of this invention, provided that the unsaturated fatty acid can be metathesized in the manner disclosed herein. An unsaturated fatty acid comprises a long carbon chain containing at least one carbon-carbon double bond and terminating in a carboxylic acid group. Typically, the unsaturated fatty acid will contain greater than about 8 carbon atoms, preferably, greater than about 10 carbon atoms, and more preferably, greater than about 12 carbon atoms. Typically, the unsaturated fatty acid will contain less than about 50 carbon atoms, preferably, less than about 35 carbon atoms, and more preferably, less than about 25 carbon atoms. At least one carbon-carbon double bond is present along the carbon chain, this double bond usually occurring about the middle of the chain, but not necessarily. The carbon-carbon double bond may also occur at any other internal location along the chain. A terminal carbon-carbon double bond, at the opposite end of the carbon chain relative to the terminal carboxylic acid group, is also suitably employed, although terminal carbon-carbon double bonds occur less commonly in fatty acids. Unsaturated fatty acids containing the terminal carboxylic acid functionality and two or more carbon-carbon double bonds may also be suitably employed in the process of this invention. Since metathesis can occur at any of the carbon-carbon double bonds, a fatty acid having more than one double bond may produce a variety of metathesis products. The unsaturated fatty acid may be straight or branched and substituted along the fatty acid chain with one or more substituents, provided that the one or more substituents are substantially inert with respect to the metathesis process. Non-limiting examples of suitable substituents include alkyl moieties, preferably $C_{1-10}$ alkyl moieties, including, for example, methyl, ethyl, propyl, butyl, and the like; cycloalkyl moieties, preferably, $C_{4-8}$ cycloalkyl moieties, including for example, cyclopentyl and cyclohexyl; monocyclic aromatic moieties, preferably, $C_6$ aromatic moieties, that is, phenyl; arylalkyl moieties, preferably, $C_{7-16}$ arylalkyl moieties, including, for example, benzyl; and alkylaryl moieties, preferably, $C_{7-16}$ alkylaryl moieties, including, for example, tolyl, ethylphenyl, xylyl, and the like; as well as hydroxyl, ether, keto, aldehyde, and halide, preferably, chloro and bromo, functionalities.

Non-limiting examples of suitable unsaturated fatty acids include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradecenoic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (godoleic), cis-1'-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), and like acids. Oleic acid is most preferred. Unsaturated fatty acids can be obtained commercially or synthesized by saponifying fatty acid esters, this method being known to those skilled in the art.

Fatty acid esters are formed by condensation of a fatty acid and an alcohol. Fatty acid alkyl esters are fatty acids where the hydrogen of the —OH of the acid group is replaced by a hydrocarbyl group, typically a $C_1$ to $C_{30}$ alkyl group, preferably a $C_1$ to $C_{20}$ alkyl.

Fatty acid alkyl esters are fatty acids where the hydrogen of the —OH of the acid group is replaced by an alkyl group. Fatty acid alkyl esters useful herein are typically represented by the formula: $R\hat{}$—C(O)—O—R*, where $R\hat{}$ is a $C_1$ to $C_{100}$ hydrocarbyl group, preferably a $C_6$ to $C_{22}$ group, preferably a $C_6$ to $C_{14}$ 1-alkene group, and R* is an alkyl group, preferably a $C_1$ to $C_{20}$ alkyl group, preferably methyl, ethyl, butyl, pentyl and hexyl. Preferred fatty acid alkyl esters useful herein are typically represented by the formula: $R\hat{}$—$CH_2$=$CH_2$—$R\hat{}$—C(O)—O—R*, where each $R\hat{}$ is, independently a $C_1$ to $C_{100}$ alkyl group, preferably a $C_6$ to $C_{20}$, preferably a $C_8$ to $C_{14}$ alkyl group, preferably a $C_9$ group and R* is an alkyl group, preferably a $C_1$ to $C_{20}$ alkyl group, preferably methyl, ethyl, butyl, pentyl and hexyl. Particularly preferred fatty acid alkyl esters useful herein are represented by the formula:

$$CH_3—(CH_2)n—C=C—(CH_2)m-C(O)—O—R*,$$

where and R* is an alkyl group, preferably a $C_1$ to $C_{20}$ alkyl group, preferably methyl, ethyl, butyl pentyl and hexyl, m and n are, independently 1, 2, 3, 4, 5, 6, 7, 8, 9, 10, 11, 12, 13, 14, 15, or 16, preferably 5, 7, 9, or 11, preferably 7.

Fatty acid methyl esters are fatty acids where the hydrogen of the —OH of the acid group is replaced by methyl group. Fatty acid methyl esters useful herein are typically represented by the formula: $R\hat{}$—C(O)—O—$CH_3$, where $R\hat{}$ is a $C_1$ to $C_{100}$ hydrocarbyl group, preferably a $C_6$ to $C_{22}$ group, preferably a $C_6$ to $C_{14}$ 1-alkene group. Preferred fatty acid methyl esters useful herein are typically represented by the formula: $R\hat{}$—$CH_2$=$CH_2$—$R\hat{}$—C(O)—O—$CH_3$, where each $R\hat{}$ is, independently a $C_1$ to $C_{100}$ alkyl group, preferably a $C_6$ to $C_{20}$, preferably a $C_8$ to $C_{14}$ alkyl group, preferably a $C_9$ group. Particularly preferred fatty acid methyl esters useful herein are represented by the formula: 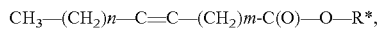C=C—$(CH_2)$m-C(O)—O$CH_3$, where m and n are, independently 1, 2, 3, 4, 5, 6, 7, 8, 9, 10, 11, 12, 13, 14, 15, or 16, preferably 5, 7, 9, or 11, preferably 7.

Preferred fatty acid methyl esters include methyl palmitoleate, methyl oleate, methyl gadoleate, methyl erucate, methyl linoleate, methyl linolenate, methyl soyate, and mixtures of methyl esters derived from soybean oil, beef tallow, tall oil, animal fats, waste oils/greases, rapeseed oil, algae oil, Canola oil, palm oil, Jathropa oil, high-oleic soybean oil (e.g., 75 mole % or more, preferably 85 mole % or more, preferably 90 mole % or more), high-oleic safflower oil (e.g., 75 mole % or more, preferably 85 mole % or more, preferably 90 mole % or more), high-oleic sunflower oil (e.g., 75 mole % or more, preferably 85 mole % or more, preferably 90 mole % or more), and other plant or animal derived sources containing fatty acids.

A preferred source of fatty acid methyl esters for use herein includes TAG's and biodiesel sources. As described above, biodiesel refers to a transesterified vegetable oil or animal fat based diesel fuel containing long-chain alkyl (typically methyl, propyl, or ethyl) esters. Biodiesel is typically made by chemically reacting lipids (such as vegetable oil) with an alcohol. Biodiesel, TAG's and derivatives thereof may be used in the processes described herein. Likewise, preferred fatty acid methyl esters useful herein may be obtained by reacting canola oil, corn oil, soybean oil, beef tallow, tall oil, animal fats, waste oils/greases, rapeseed oil, algae oil, Canola oil, palm oil, Jathropa oil, high-oleic soybean oil, high-oleic safflower oil, high-oleic sunflower oil or mixtures of animal and/or vegetable fats and oils with one or more alcohols (as described above), preferably methanol.

Vegetable oils useful herein preferably contain at least one site of unsaturation and include, but are not limited to, canola, soybean, palm, peanut, mustard, sunflower, tung, tall, perilla, grapeseed, rapeseed, linseed, safflower, pumpkin corn and other oils extracted from plant seeds.

For purposes of this invention and the claims thereto the term "seed oil" refers to one or more vegetable or animal oils, such as canola oil, corn oil, soybean oil, beef tallow, tall oil, animal fats, waste oils/greases, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and/or vegetable fats and oils, castor bean oil, dehydrated castor bean oil, cucumber oil, poppyseed oil, flaxseed oil, lesquerella oil, walnut oil, cottonseed oil, meadowfoam, tuna oil, and sesame oils.

In a preferred embodiment, a combination of oils is used herein. Preferred combinations include two (three or four) or more of tall oil, palm oil, tallow, waste grease, rapeseed oil, canola oil, soy oil and algae oil. Alternate useful combinations include two (three or four) or more of soy oil, canola oil, rapeseed oil, algae oil, and tallow.

In certain embodiments processed oils, such as blown oils, are the source of fatty acids useful herein. While vegetable oils are preferred sources of fatty acids for practicing disclosed embodiments of the present process, fatty acids also are available from animal fats including, without limitation, lard and fish oils, such as sardine oil and herring oil, and the like. As noted above, in certain embodiments a desired fatty acid or fatty acid precursor is produced by a plant or animal found in nature. However, particular fatty acids or fatty acid precursors are advantageously available from genetically modified organisms, such as a genetically modified plants, particularly genetically modified algae. Such genetically modified organisms are designed to produce a desired fatty acid or fatty acid precursor biosynthetically or to produce increased amounts of such compounds.

Alkyl oleates and alkyl erucates are fatty acid esters that are often major components in biodiesel produced by the trans-esterification of alcohol and vegetable oils. (preferably the alkyls are a $C_1$ to $C_{30}$ alkyl group, alternately a $C_1$ to $C_{20}$ alkyl group.) Biodiesel compositions that are particularly useful in this invention are those which have high concentrations of alkyl oleate and alkyl erucate esters. These fatty acid esters preferably have one site of unsaturation such that cross-metathesis with ethylene yields 1-decene as the coproduct. Biodiesel compositions that are particularly useful are those produced from vegetable oils such as canola, rapeseed oil, palm oil, and other high oleate oil, high erucate oils. Particularly preferred vegetable oils include those having at least 50% (on a molar basis) combined oleic and erucic fatty acid chains of all fatty acid chains, preferably 60%, preferably 70%, preferably 80%, preferably 90%.

In another embodiment, useful fatty acid ester containing mixtures include those having at least 50% (on a molar basis) alkyl oleate fatty acid esters, preferably 60% of alkyl oleate fatty acid esters, preferably 70% of alkyl oleate fatty acid esters, preferably 80% of alkyl oleate fatty acid esters, preferably 90% of alkyl oleate fatty acid esters.

In another embodiment, useful fatty acid ester containing mixtures include those having at least 50% (on a molar basis) alkyl erucate fatty acid esters, preferably 60% of alkyl erucate fatty acid esters, preferably 70% of alkyl erucate fatty acid esters, preferably 80% of alkyl erucate fatty acid esters, preferably 90% of alkyl erucate fatty acid esters.

In another embodiment, useful fatty acid ester containing mixtures include those having at least 50% (on a molar basis) combined oleic and erucic fatty acid esters of all fatty acid ester chains, preferably 60% preferably 70%, preferably 80%, preferably 90%.

Isomerization

In another embodiment, the feed material is first isomerized, then combined with a metathesis catalyst as described herein. For example, the processes disclosed herein may comprise providing a feed material (typically a fatty acid or fatty acid derivative), isomerizing a site of unsaturation in the feed material (typically a fatty acid or fatty acid derivative) to produce an isomerized feed material (typically a fatty acid or fatty acid derivative), and then contacting the isomerized material with an alkene in the presence of a metathesis catalyst. The isomerized material can be produced by isomerization with or without subsequent esterification or transesterification. Isomerization can be catalyzed by known biochemical or chemical techniques. For example, an isomerase enzyme, such as a linoleate isomerase, can be used to isomerize linoleic acid from the cis 9, c is 12 isomer to the cis 9, bans 11 isomer. This isomerization process is stereospecific, however, nonstereospecific processes can be used because both cis and trans isomers are suitable for metathesis. For example, an alternative process employs a chemical isomerization catalyst, such as an acidic or basic catalyst, can be used to isomerize an unsaturated feed material (typically a fatty acid or fatty acid derivative) having a site of unsaturation at one location in the molecule into an isomerized, feed material (typically a fatty acid or fatty acid derivative) having a site of unsaturation at a different location in the molecule. Metal or organometallic catalysts also can be used to isomerize an unsaturated feed material (typically a fatty acid or fatty acid derivative). For example, nickel catalysts are known to catalyze positional isomerization of unsaturated sites in fatty acid derivatives. Similarly, esterification, transesterification, reduction, oxidation and/or other modifications of the starting compound or products, such as a fatty acid or fatty acid derivative, can be catalyzed by biochemical or chemical techniques. For example, a fatty acid or fatty acid derivative can be modified by a lipase, esterase, reductase or other enzyme before or after isomerization. In another embodiment the isomerization described above may be practiced with any triacylglycerides, biodiesel, fatty acids, fatty acid esters and/ or fatty acid alkyl esters described herein, typically before contacting with the metathesis catalyst.

Metathesis Catalysts

In a preferred embodiment, the metathesis catalyst is represented by the formula:

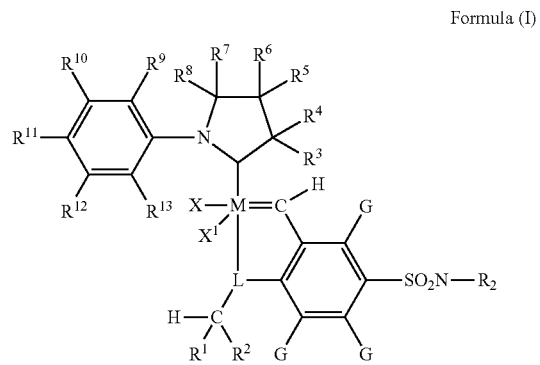

Formula (I)

where:

M is a Group 8 metal, preferably Ru or Os, preferably Ru;

X and $X^1$ are, independently, any anionic ligand, preferably a halogen (preferably $C_1$), an alkoxide or an alkyl sulfonate, or X and $X^1$ may be joined to form a dianionic group and may form single ring of up to 30 non-hydrogen atoms or a multinuclear ring system of up to 30 non-hydrogen atoms;

L is N, O, P, or S, preferably N or O;

R is hydrogen or a $C_1$ to $C_{30}$ hydrocarbyl or substituted hydrocarbyl, preferably methyl; $R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl, preferably methyl, ethyl, propyl or butyl, preferably $R^1$, $R^2$, $R^3$, and Ware methyl;

each $R^9$ and $R^{13}$ are, independently, hydrogen or a $C_1$ to $C_{30}$ hydrocarbyl or substituted hydrocarbyl, preferably a $C_2$ to $C_6$ hydrocarbyl, preferably ethyl;

$R^{10}$, $R^{11}$, $R^{12}$ are, independently, hydrogen or a $C_1$ to $C_{30}$ hydrocarbyl or substituted hydrocarbyl, preferably hydrogen or methyl;

each G, is, independently, hydrogen, halogen or $C_1$ to $C_{30}$ substituted or unsubstituted hydrocarbyl (preferably a $C_1$ to $C_{30}$ substituted or unsubstituted alkyl or a substituted or unsubstituted $C_4$ to $C_{30}$ aryl);

where any two adjacent R groups may form a single ring of up to 8 non-hydrogen atoms or a multinuclear ring system of up to 30 non-hydrogen atoms.

Preferably any two adjacent R groups may form a fused ring having from 5 to 8 non hydrogen atoms. Preferably the non-hydrogen atoms are C and or O. Preferably the adjacent R groups form fused rings of 5 to 6 ring atoms, preferably 5 to 6 carbon atoms. By adjacent is meant any two R groups located next to each other, for example $R^3$ and $R^4$ can form a ring and/or $R^{11}$ and $R^{12}$ can form a ring.

In a preferred embodiment, at least one of $R^9$ and $R^{13}$ is a $C_1$ to $C_{30}$ hydrocarbyl or substituted hydrocarbyl, preferably both are $C_1$ to $C_{30}$ hydrocarbyl or substituted hydrocarbyl.

For purposes of this invention and claims thereto a substituted hydrocarbyl is a radical made of carbon and hydrogen where at least one hydrogen is replaced by a heteroatom. For purposes of this invention and claims thereto a substituted alkyl or aryl group is a radical made of carbon and hydrogen where at least one hydrogen is replaced by a heteroatom or a linear, branched, or cyclic substituted or unsubstituted hydrocarbyl group having 1 to 30 carbon atoms.

Preferred alkoxides include those where the alkyl group is a phenol, substituted phenol (where the phenol may be substituted with up to 1, 2, 3, 4 or 5 $C_1$ to $C_{1-2}$ hydrocarbyl groups) or a $C_1$ to $C_{10}$ hydrocarbyl, preferably a $C_1$ to $C_{10}$ alkyl group, preferably methyl, ethyl, propyl, butyl, or phenyl.

Preferred alkyl sulfonates are represented by the Formula (II):

Formula (II)

where $R^2$ is a $C_1$ to $C_{30}$ hydrocarbyl group, fluoro-substituted carbyl group, chloro-substituted carbyl group, aryl group, or substituted aryl group, preferably a $C_1$ to $C_{12}$ alkyl or aryl group, preferably trifluoromethyl, methyl, phenyl, para-methyl-phenyl.

Preferred metathesis catalysts include: 2-(2,6-diethylphenyl)-3,5,5,5-tetramethylpyrrolidine[2-(i-propoxy)-5-(N,N-dimethylaminosulfonyl)phenyl]methylene ruthenium dichloride; 2-(mesityl)-3,3,5,5-tetramethylpyrrolidine[2-(i-propoxy)-5-(N,N-dimethylaminosulfonyl)phenyl]methylene ruthenium dichloride; 2-(2-isopropyl)-3,3,5,5-tetramethylpyrrolidine[2-(i-propoxy)-5-(N,N-dimethylaminosulfonyl)phenyl]methylene ruthenium dichloride; 2-(2,6-diethyl-4-fluorophenyl)-3,3,5,5-tetramethylpyrrolidine[2-(i-propoxy)-5-(N,N-dimethylaminosulfonyl)phenyl]methylene ruthenium dichloride, and mixtures thereof.

The catalyst compounds described herein may be synthesized as follows.

The cyclic (alkyl)(amino)carbene precursor, as the aldiminium salt, can be synthesized as reported in the literature (Angew Chem. Int. Ed. 2005, 44, 5705-5709 or in WO 2006/138166). For example 2,6-diethylaniline is reacted with isobutyraldehyde in the presence of 3 angstrom molecular sieves and a catalytic amount of p-toluenesulfonic acid monohydrate at 50° C. in benzene. The resulting imine is reacted with a deprotonating agent such as lithium diisopropyl amide which is reacted with 1,2-epoxy-2-methylpropane. Treatment with trifluoromethane sulfonic anhydride yields the aldiminium salt. The aldiminium salt upon deprotonation with the appropriate base such as potassium bistrimethylsilyl amide generates the carbene at low temperatures such as –80° C. This carbene can be reacted with ruthenium alkylidene complexes such as 2-(i-propoxy)-5-(N,N-dimethylaminosulfonyl)phenyl]methylene}(tricyclohexylphosphine) ruthenium dichloride to generate the cyclic alky amino carbene ruthenium complex, 2-(2,6-diethylphenyl)-3,3,5,5-tetramethylpyrrolidine[2-(i-propoxy)-5-(N,N-dimethylaminosulfonyl)phenyl]methylene ruthenium dichloride.

The resulting ruthenium alkylidene complex is an efficient catalyst or catalyst precursor towards for the cometathesis of ethylene and methyl oleate, a component of biodiesel, to generate with good selectivity 1-decene and methyl-9-decenoate. The co-metathesis reaction is performed in a suitable solvent such as dichloromethane, toluene, hexane, or other analogous solvents. The reaction is performed at 40 to 50° C., and may be performed at a temperature range of 0° C. to 100° C. The ethylene pressure in the reaction vessel is typically in a range of 100 to 200 psi. It may be in a range of 10 psi to 1000 psi of ethylene.

Alpha-Olefin Products of the Metathesis Reaction.

In a preferred embodiment, the processes described herein produce a linear alpha olefin. The alpha-olefin, preferably linear alpha-olefin, produced herein contains at least one more carbon than the alkene used in the reaction to make the alpha-olefin.

In another embodiment, the processes described herein produce a blend of an alpha olefin and an ester-functionalized alpha olefin. Generally a mixture of non-ester-containing alpha olefins will be produced due to the presence of mono-, di-, and tri-unsubstituted fatty acid chains. The major alpha olefin products are expected to be 1-decene, 1-heptene, and 1-butene. The major ester-containing alpha olefin product is methyl dec-9-enoate.

In a preferred embodiment, the alpha olefin produced herein is 1-decene. Typically the 1-decene is produced with an ester.

In a preferred embodiment, the major alpha olefin produced herein is 1-decene. Typically the 1-decene is produced with an ester.

In a preferred embodiment, ethylene and methyl oleate are combined with the metathesis catalysts described herein (such as 2-(2,6-diethylphenyl)-3,3,5,5-tetramethylpyrrolidine[2-(i-propoxy)-5-(N,N-dimethylaminosulfonyl)phenyl] methylene ruthenium dichloride) to produce 1-decene and methyl dec-9-enoate.

Separation of the 1-olefin (such as the 1-decene) from the ester may be by means typically known in the art such as distillation or filtration.

The linear alpha-olefin (such as 1-decene or a mixture of $C_8$, $C_{10}$, $C_{12}$ linear alpha olefins) is then separated from any esters present and preferably used to make poly-alpha-olefins (PAOs). Specifically, PAOs may be produced by the polymerization of olefin feed in the presence of a catalyst such as $AlCl_3$, $BF_3$, or $BF_3$ complexes. Processes for the production of PAOs are disclosed, for example, in the following patents: U.S. Pat. Nos. 3,149,178; 3,382,291; 3,742,082; 3,769,363; 3,780,128; 4,172,855 and 4,956,122, which are fully incorporated by reference. PAOs are also discussed in: Will, J. G. Lubrication Fundamentals, Marcel Dekker New York, 1980. Certain high viscosity index PAO's may also be conveniently made by the polymerization of an alpha-olefin in the presence of a polymerization catalyst such as Friedel-Crafts catalysts. These include, for example, aluminum trichloride, boron trifluoride, aluminum trichloride or boron trifluoride promoted with water, with alcohols such as ethanol, propanol, or butanol, with carboxylic acids, or with esters such as ethyl acetate or ethyl propionate or ether such as diethyl ether, diisopropyl ether, etc., see for example, the methods disclosed by U.S. Pat. Nos. 4,149,178; 3,382,291; 3,742,082; 3,769,363 (Brennan); 3,876,720; 4,239,930; 4,367,352; 4,413,156; 4,434,408; 4,910,355; 4,956,122; 5,068,487; 4,827,073; 4,827,064; 4,967,032; 4,926,004; and 4,914,254. PAO's can also be made using various metallocene catalyst systems. Examples include U.S. Pat. No. 6,706,828; WO 96/23751; EP 0 613 873; U.S. Pat. No. 5,688,887; U.S. Pat. No. 6,043,401; WO 03/020856; U.S. Pat. No. 6,548,724; U.S. Pat. No. 5,087,788; U.S. Pat. No. 6,414,090; U.S. Pat. No. 6,414,091; U.S. Pat. No. 4,704,491; U.S. Pat. No. 6,133,209; and U.S. Pat. No. 6,713,438.

PAOs are often used as additives and base stocks for lubricants, among other things. Additional information on the use of PAO's in the formulations of full synthetic, semi-synthetic or part synthetic lubricant or functional fluids can be found in "Synthetic Lubricants and High-Performance Functional Fluids", 2nd Ed. L. Rudnick, etc. Marcel Dekker, Inc., N.Y. (1999). Additional information on additives used in product formulation can be found in "Lubricants and Lubrications, Ed. By T. Mang and W. Dresel, by Wiley-VCH GmbH, Weinheim 2001.

In another embodiment this invention relates to:
1. A metathesis catalyst compound represented by the formula:

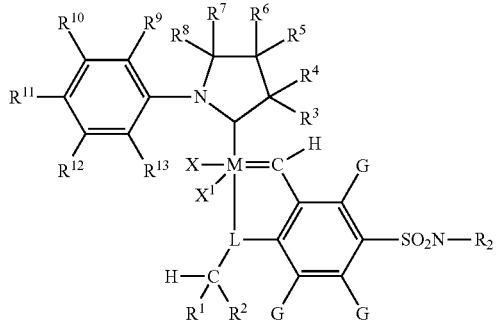

where:
M is a Group 8 metal;
X and $X^1$ are, independently, any anionic ligand, or X and $X^1$ may be joined to form a dianionic group and may form single ring of up to 30 non-hydrogen atoms or a multinuclear ring system of up to 30 non-hydrogen atoms;
L is N, O P, or S;
R is hydrogen or a $C_1$ to $C_{30}$ hydrocarbyl or substituted hydrocarbyl;
$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;
each $R^9$ and $R^{13}$ are, independently, hydrogen, a $C_1$ to $C_{30}$ hydrocarbyl or substituted hydrocarbyl;
$R^{10}$, $R^{11}$, $R^{12}$ are, independently, hydrogen or a $C_1$ to $C_{30}$ hydrocarbyl or substituted hydrocarbyl;
each G, is, independently, hydrogen, halogen or $C_1$ to $C_{30}$ substituted or unsubstituted hydrocarbyl;
where any two adjacent R groups may form a single ring of up to 8 non-hydrogen atoms or a multinuclear ring system of up to 30 non-hydrogen atoms.
2. The catalyst compound of paragraph 1, wherein M is ruthenium.
3. The catalyst compound of paragraph 1 or 2, wherein X and $X^1$ are, independently, a halogen, an alkoxide or an alkyl sulfonate.
4. The catalyst compound of any of paragraphs 1 to 3, wherein X and $X^1$ are Cl.
5. The catalyst compound of any of paragraphs 1 to 4, wherein L is N or O.
6. The catalyst compound of any of paragraphs 1 to 5, wherein R is a $C_1$ to $C_{30}$ hydrocarbyl.
7. The catalyst compound of any of paragraphs 1 to 6, wherein R is methyl.
8. The catalyst compound of any of paragraphs 1 to 7, wherein each G is independently, a $C_1$ to $C_{30}$ substituted or unsubstituted alkyl, or a substituted or unsubstituted $C_4$ to $C_{30}$ aryl.
9. The catalyst compound of any of paragraphs 1 to 8, wherein L is N.
10. The catalyst compound of paragraph 1, wherein the metathesis catalyst compound comprises one or more of: 2-(2,6-diethylphenyl)-3,5,5,5-tetramethylpyrrolidine[2-(i-propoxy)-5-(N,N-dimethylaminosulfonyl)phenyl]methylene ruthenium dichloride; 2-(mesityl)-3,3,5,5-tetramethylpyrrolidine[2-(i-propoxy)-5-(N,N-dimethylaminosulfonyl)phenyl]methylene ruthenium dichloride; 2-(2-isopropyl)-3,3,5,5-tetramethylpyrrolidine[2-(i-propoxy)-5-(N,N-dimethylaminosulfonyl)phenyl]methylene ruthenium dichloride; 2-(2,6-diethyl-4-fluorophenyl)-3,3,5,5-tetramethylpyrrolidine[2-(i-propoxy)-5-(N,N-dimethylaminosulfonyl)phenyl]methylene ruthenium dichloride, or mixtures thereof.
11. A process to produce alpha-olefin comprising contacting a seed oil with the catalyst compound of any of paragraphs 1 to 10.
12. The process of paragraph 11, wherein the seed oil is selected from the group consisting of canola oil, corn oil, soybean oil, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils and mixtures thereof.
13. The process of paragraph 11, wherein the seed oil is selected from the group consisting of palm oil and algae oil.
14. A process to produce alpha-olefin comprising contacting a triacylglyceride with an alkene and the catalyst compound of any of paragraphs 1 to 10, preferably wherein the alpha olefin produced has at least one more carbon atom than the alkene.
15. The process of paragraph 14, wherein the triacylglyceride is contacted with alcohol and converted to an fatty acid ester or fatty acid alkyl ester prior to contacting with the catalyst compound of any of paragraphs 1 to 10.
16. The process of paragraph 14, wherein the triacylglyceride is contacted with water or an alkaline reagent and converted to a fatty acid prior to contacting with the catalyst compound of any of paragraphs 1 to 10.
17. A process to produce alpha-olefin comprising contacting an unsaturated fatty acid with an alkene and the catalyst compound of any of paragraphs 1 to 10, preferably wherein the alpha olefin produced has at least one more carbon atom than the alkene.
18. A process to produce alpha-olefin comprising contacting a triacylglyceride with the catalyst compound of any of paragraphs 1 to 10, preferably wherein the alpha olefin produced has at least one more carbon atom than the alkene.
19. A process to produce alpha-olefin comprising contacting an unsaturated fatty acid ester and or unsaturated fatty acid alkyl ester with an alkene and the catalyst compound of any of paragraphs 1 to 10, preferably wherein the alpha olefin produced has at least one more carbon atom than the alkene.
20. The process of any of paragraphs 11 to 19, wherein the alpha olefin is a linear alpha-olefin having 4 to 24 carbon atoms.
21. The process of any of paragraphs 11 to 20, wherein the alkene is ethylene, propylene, butene, hexene or octene.
22. The process of any of paragraphs 19 to 21, wherein the fatty acid ester is a fatty acid methyl ester.
23. The process of any of paragraphs 14 to 22, wherein the triacylglyceride, fatty acid, fatty acid alkyl ester, fatty acid ester is derived from biodiesel.
24. The process of any of paragraphs 11 to 23, wherein the alpha-olefin is butene-1, decene-1 and or heptene-1.
25. The process of any of paragraphs 11 to 24, wherein the productivity of the process is at least 200 g of linear alpha-olefin per mmol of catalyst per hour.
26. The process of any of paragraphs 11 to 25, wherein the selectivity of the process is at least 20 wt % linear alpha-olefin, based upon the weight to the material exiting the reactor.
27. The process of any of paragraphs 11 to 26, wherein the turnover number, defined as the moles of alpha olefin formed per mol of catalyst, of the process is at least 10,000.

28. The process of any of paragraphs 11 to 27, wherein the yield, when converting unsaturated fatty acids, unsaturated fatty acid esters, unsaturated fatty acid alkyl esters or mixtures thereof, is 30% or more, said yield being defined as defined as the moles of alpha olefin formed per mol of unsaturated fatty acids, unsaturated fatty acid esters, unsaturated fatty acid alkyl esters or mixtures thereof introduced into the reactor.

29. The process of any of paragraphs 11 to 27, wherein the yield, when converting TAGs as represented in the formula below, is 30% or more, said yield being defined as defined as the moles of alpha olefin formed divided by (the moles of unsaturated $R^a$+moles of unsaturated $R^b$+moles of unsaturated $R^c$) introduced into the reactor,

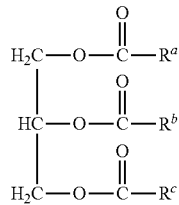

where $R^a$, $R^b$ and $R^c$ each, independently, represent a saturated or unsaturated hydrocarbon chain.

30. The process of paragraph 28, wherein the yield is 60% or more.

31. A process to produce $C_4$ to $C_{24}$ linear alpha-olefin comprising contacting a feed material with an alkene selected from the group consisting of ethylene, propylene butene, pentene, hexene, heptene, octene, nonene and mixtures thereof and a metathesis catalyst compound of any of paragraphs 1 to 10, wherein the feed material is a triacylglyceride, fatty acid, fatty acid alkyl ester, and/or fatty acid ester derived from seed oil.

32. The process of paragraph 31, wherein the alkene is ethylene, the alpha olefin is 1-butene, 1-heptene and or -decene, and the feed material is a fatty acid methyl ester, and/or fatty acid ester.

EXPERIMENTAL SECTION

Tests and Materials

All molecular weights are number average unless otherwise noted. All molecular weights are reported in g/mol unless otherwise noted.

THF is tetrahydrofuran.

Products were analyzed by gas chromatography (Agilent 6890N with auto-injector) using helium as a carrier gas at 38 cm/sec. A column having a length of 60 m(J & W Scientific DB-1, 60 m×0.25 mm I.D.×1.0 μm film thickness) packed with a flame ionization detector (FID), an Injector temperature of 250° C., and a Detector temperature of 250° C. were used. The sample injected into the column in an oven at 70° C., then heated to 275° C. over 22 minutes (ramp rate 10° C./min to 100° C., 30° C./min to 275° C., hold).

Examples

Synthesis Example 1

Synthesis of (E)-2,6-diethyl-N-(2-methylpropylidene) aniline (compound 1). Benzene (150 mL) was added to 2,6-diethylaniline (18.59 g, 124.6 mmol) and 3 angstrom molecular sieves (ca. 50 mL). Then isobutyraldehyde (9.43 g, 131 mmol) and p-toluenesulfonic acid monohydrate (20 mg, 0.011 mmol) were added. The flask was sealed and heated to 50° C. After stirring overnight the very pale yellow solution was filtered and the volatiles were removed under reduced pressure to afford the product as a clear, pale yellow oil. Yield: 22.5 g, 84.6%. $^1$H NMR ($C_6D_6$): δ 7.21 (1H, d), 7.02 (2H, m), 2.47 (4H, q), 2.39 (1H, m), 1.11 (6H, t), 1.01 (6H, d).

Synthesis of lithium (2,6-diethylphenyl)(2-methylprop-1-enyl)amide (compound 2). Benzene (70 mL) and compound 1 (6.63 g, 32.6 mmol) were combined. Then solid lithium diisopropylamide (4.01 g, 37.4 mmol) was added. The mixture was heated to 50° C. to form a cloudy red-orange solution. After a few hours the solution was filtered through diatomaceous earth to afford a clear yellow solution. The volatiles were evaporated to give a yellow solid. Pentane (15 mL) was added and the mixture was stirred briefly and then cooled to −10° C. overnight. The product was then collected on a glass frit and washed with pentane (2×20 mL) to give a white solid that was dried under reduced pressure. Yield: 5.50 g, 80.6%.

Synthesis of 1-(2,6-diethylphenyl)-2,2,4,4-tetramethyl-3,4-dihydro-2H-pyrrolium triflate (compound 3). $Et_2O$ (100 mL) was added to compound 2 (5.50 g, 26.3 mmol) to form a clear yellow solution. An $Et_2O$ (5 mL) solution of 1,2-epoxy-2-methylpropane (1.90 g, 26.3 mmol) was added dropwise over about 10 seconds, and the mixture was stirred overnight. The next day the mixture was cooled to −80° C. and trifluoromethanesulfonic anhydride (7.42 g, 26.3 mmol) was added dropwise. The mixture was warmed to ambient temperature over 1 hour. A thick suspension formed. After stirring for an additional hour, the solid was collected on a glass frit and washed with $Et_2O$ (3×15 mL). The solid was dried under reduced pressure. This was then extracted with $CH_2Cl_2$ (60 mL) and filtered through diatomaceous earth. The filter cake was washed with $CH_2Cl_2$ (2×30 mL). The combined $CH_2Cl_2$ extracts were evaporated to an oil and $Et_2O$ (15 mL) was added to cause a white crystalline solid to form. The solution was cooled to −10° C. overnight. The solid was then collected and dried under reduced pressure to afford 1.48 g of product. To obtain additional product the filter cake was loaded into a thimble. This was placed in a Soxhlet extractor and the solid was extracted with hot $CH_2Cl_2$ overnight. The resulting $CH_2Cl_2$ extract was evaporated and $Et_2O$ (10 mL) was added to afford additional product as off-white crystals. Total yield: 3.28 g, 30.6%. $^1$H NMR($C_6D_6$): δ 7.21 (1H, d), 7.02 (2H, m), 2.47 (4H, q), 2.39 (1H, m), 1.11 (6H, t), 1.01 (6H, d).

Synthesis of 2-(2,6-diethylphenyl)-3,3,5,5-tetramethylpyrrolidine[2-(i-propoxy)-5-(N,N-dimethylaminosulfonyl)phenyl]methylene ruthenium dichloride (compound 4). Tetrahydrofuran (40 mL) was added to KN(SiMe3)$_2$ (0.379 g, 1.90 mmol) to form a homogeneous solution. At −80° C. solution of compound 3 (0.775 g, 1.90 mmol) and THF (10 mL) was added dropwise over about 10 seconds. After 30 seconds a THF (10 mL) solution of {[2-(i-propoxy)-5-(N,N-dimethyl-aminosulfonyl)phenyl]methylene}-(tricyclohexylphosphine) ruthenium dichloride (0.612 g, 0.865 mmol), which had been cooled to −10° C., was added dropwise over about 15 seconds. The mixture was stirred for 10 minutes then warmed to ambient temperature. The mixture was then stirred for 2 h, then the volatiles were removed under reduced pressure. The residue was extracted with 20 mL of a 3:2 mixture of hexane:$CH_2Cl_2$ and filtered. This solution was loaded on to a $SiO_2$ column (1.25"×8") that had been packed with the same solvent mixture. The column was eluted with 3:2 hexane: $CH_2Cl_2$ (300 mL) and then the solvent strength was gradually increased to pure $CH_2Cl_2$. The product eluted as a dark green band. Removal of the volatiles afforded a dark green oil that crystallized upon the addition of pentane (2 mL) and cooling to −10° C. overnight. The product was isolated as green flocculent crystals that were dried under reduced pressure (0.038 g, 6.4%). $^1$H NMR (CD$_2$Cl$_2$): δ 16.26 (1H, s, RuCH—), 7.96 (1H, dd), 7.64 (1H, t), 7.47 (2H, d), 7.18 (1H, d, J=2 Hz), 7.11 (1H, d), 5.22 (1H, sept), 2.64 (6H, s), 2.53 (4H, m), 2.19 (2H, s), 2.07 (6H, s), 1.77 (6H, d), 1.32 (6H, s), 0.88 (6H, t).

Cross Metathesis of Methyl Oleate with Ethylene

Example 1

A stock solution was made by dissolving 4.5 mg of 2-(2,6-diethylphenyl)-3,3,5,5-tetramethylpyrrolidine[2-(i-propoxy)-5-(N,N-dimethylaminosulfonyl) phenyl]methylene ruthenium dichloride in 25 mL anhydrous dichloromethane. 1.0 mL (0.87 g) methyl oleate, 1.26 g (125 nmol catalyst) of catalyst stock solution, 3.7 g anhydrous dichloromethane, and 0.152 g (0.2 mL) tetradecane as an internal standard were weighed out and then placed in a Fisher-Porter bottle equipped with a stir bar. The vessel was then filled with ethylene to 150 psig (1034 kPa) and placed in an oil bath heated to 40° C. for 2 hours. After completion the vessel was depressurized and approximately 0.5 mL ethyl vinyl ether was added to stop the reaction. A sample was then taken and analyzed by GC as described above.

Example 2

This example was run according to the procedure in Example 1, except that the amount of catalyst for this run was halved such that 0.63 g (62.5 nmol catalyst) of catalyst stock solution was added along with 4.4 g anhydrous dichloromethane. The amount of methyl oleate (1.0 mL, 0.876 g) and tetradecane standard (0.2 mL, 0.152 g) remained the same. The reactants were placed in a Fisher-Porter bottle and into a 40° C. oil bath for 2 hours, after which ethyl vinyl ether was added to stop the reaction. A sample was taken and analyzed by GC as described above.

Example 3

This example was run according to the procedure in Example 2, except that the amount of catalyst was for this run was halved from the previous run to 0.31 g (31.25 nmol catalyst) of catalyst stock solution which was added along with 4.7 g anhydrous dichloromethane. The amount of methyl oleate and internal standard remained the same. The reactants were placed in a Fisher-Porter bottle and into a 40° C. oil bath for 2 hours, after which ethyl vinyl ether was added to stop the reaction. A sample was taken and analyzed by GC as described above.

Example 4

This example was run according to the procedure in Example 3, except that the catalyst loading was halved once more to 0.157 g (15.62 nmol catalyst) of catalyst stock solution along with 4.9 g anhydrous dichloromethane. Methyl oleate and standard amounts remained the same. The reactants were placed in a Fisher-Porter bottle and into a 40° C. oil bath for 2 hours, after which ethyl vinyl ether was added to stop the reaction. A sample was taken and analyzed by GC as described above.

Example 5

This example was run according to the procedure in Example 4, expect that the catalyst loading was increased to 0.235 g (23.43 nmol catalyst) of stock solution with 4.8 g anhydrous dichloromethane. Methyl oleate and standard amounts remained the same. The reactants were placed in a Fisher-Porter bottle and into a 40° C. oil bath for 2 hours, after which ethyl vinyl ether was added to stop the reaction. A sample was taken and analyzed by GC as described above.

In Table 2, % yield is shown as a percentage and defined as 100×[micromoles of 1-decene]/[micromoles of methyl oleate weighed into reactor]. 1-decene selectivity is shown as a percentage and is defined as 100×[peak area of 1-decene and methyl-9-decenoate]/[sum of peak areas of 1-decene, methyl-9-decenoate, and the homometathesis products, 9-octadecene, and 1,18-dimethyl-9-octadecenedioate]. Catalyst turnover for production of the 1-decene is defined as the [micromoles of 1-decene]/([micromoles of catalyst].

TABLE 2

| Reaction conditions, 40° C., 2 hours | | | |
|---|---|---|---|
| Example | nmoles Catalyst | % Selectivity | % Yield | No. Turnovers 1-Decene |
| 1 | 125 | 92.0 | 62.8 | 14,700 |
| 2 | 62.5 | 88.2 | 52.9 | 24,800 |
| 3 | 31.25 | 90.2 | 46.7 | 43,840 |
| 5 | 23.43 | 92.4 | 43.6 | 52,400 |
| 4 | 15.62 | 91.0 | 31.7 | 59,400 |

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What we claim is:

1. A metathesis catalyst compound represented by the formula:

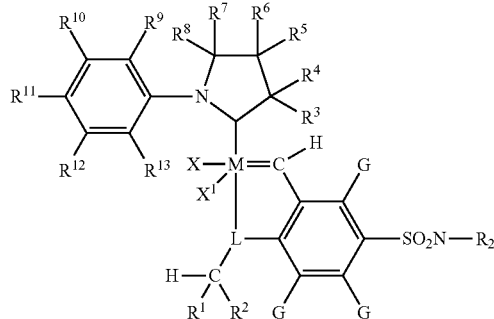

where:

M is a Group 8 metal;

X and X$^1$ are, independently, any anionic ligand, or X and X$^1$ may be joined to form a dianionic group and may form single ring of up to 30 non-hydrogen atoms or a multinuclear ring system of up to 30 non-hydrogen atoms;

L is N, O P, or S;

R is hydrogen or a $C_1$ to $C_{30}$ hydrocarbyl or substituted hydrocarbyl;

$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;

each $R^9$ and $R^{13}$ are, independently, hydrogen, a $C_1$ to $C_{30}$ hydrocarbyl or substituted hydrocarbyl;

$R^{10}$, $R^{11}$, $R^{12}$ are, independently, hydrogen or a $C_1$ to $C_{30}$ hydrocarbyl or substituted hydrocarbyl;

each G, is, independently, hydrogen, halogen or $C_1$ to $C_{30}$ substituted or unsubstituted hydrocarbyl; and where any two adjacent R groups may form a single ring of up to 8 non-hydrogen atoms or a multinuclear ring system of up to 30 non-hydrogen atoms.

2. The catalyst compound of claim 1, wherein M is ruthenium.

3. The catalyst compound of claim 1, wherein X and $X^1$ are, independently, a halogen, an alkoxide or a alkyl sulfonate.

4. The catalyst compound claim 1, wherein X and $X^1$ are Cl.

5. The catalyst compound of claim 1, wherein L is N or O.

6. The catalyst compound of claim 1, wherein R is a $C_1$ to $C_{30}$ hydrocarbyl.

7. The catalyst compound of claim 1, wherein R is methyl.

8. The catalyst compound of claim 1, wherein each G is independently, a $C_1$ to $C_{30}$ substituted or unsubstituted alkyl, or a substituted or unsubstituted $C_4$ to $C_{30}$ aryl.

9. The catalyst compound of claim 2, wherein L is N.

10. The catalyst compound of claim 1, wherein the metathesis catalyst compound comprises one or more of:

2-(2,6-diethylphenyl)-3,5,5,5-tetramethylpyrrolidine[2-(i-propoxy)-5-(N,N-dimethylaminosulfonyl)phenyl]methylene ruthenium dichloride; 2-(mesityl)-3,3,5,5-tetramethylpyrrolidine[2-(i-propoxy)-5-(N,N-dimethylaminosulfonyl)phenyl]methylene ruthenium dichloride; 2-(2-isopropyl)-3,3,5,5-tetramethylpyrrolidine[2-(i-propoxy)-5-(N,N-dimethylaminosulfonyl)phenyl]methylene ruthenium dichloride; 2-(2,6-diethyl-4-fluorophenyl)-3,3,5,5-tetramethylpyrrolidine[2-(i-propoxy)-5-(N,N-dimethylaminosulfonyl)phenyl]methylene ruthenium dichloride, or mixtures thereof.

11. A process to produce alpha-olefin comprising contacting a feed oil with a metathesis catalyst compound represented by the formula:

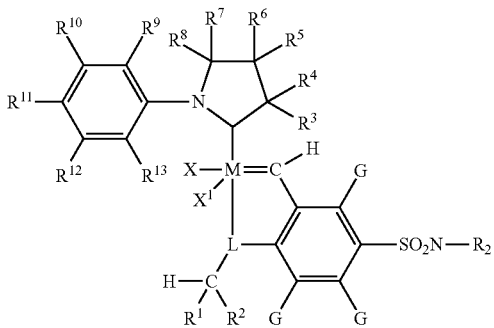

where:

M is a Group 8 metal;

X and $X^1$ are, independently, any anionic ligand, or X and $X^1$ may be joined to form a dianionic group and may form single ring of up to 30 non-hydrogen atoms or a multinuclear ring system of up to 30 non-hydrogen atoms;

L is N, O P, or S;

R is hydrogen or a $C_1$ to $C_{30}$ hydrocarbyl or substituted hydrocarbyl;

$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;

each $R^9$ and $R^{13}$ are, independently, hydrogen, a $C_1$ to $C_{30}$ hydrocarbyl or substituted hydrocarbyl;

$R^{10}$, $R^{11}$, $R^{12}$ are, independently, hydrogen or a $C_1$ to $C_{30}$ hydrocarbyl or substituted hydrocarbyl;

each G, is, independently, hydrogen, halogen or $C_1$ to $C_{30}$ substituted or unsubstituted hydrocarbyl; and where any two adjacent R groups may form a single ring of up to 8 non-hydrogen atoms or a multinuclear ring system of up to 30 non-hydrogen atoms.

12. The process of claim 11, wherein the feed oil is a seed oil is selected from the group consisting of canola oil, corn oil, soybean oil, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils and mixtures thereof.

13. The process of claim 11, wherein the feed oil is selected from the group consisting of palm oil and algae oil.

14. A process to produce alpha-olefin comprising contacting a triacylglyceride with an alkene and a metathesis catalyst compound represented by the formula:

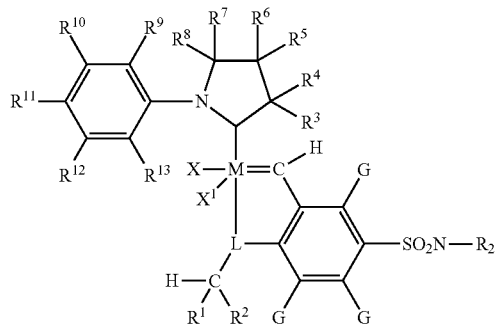

where:

M is a Group 8 metal;

X and $X^1$ are, independently, any anionic ligand, or X and $X^1$ may be joined to form a dianionic group and may form single ring of up to 30 non-hydrogen atoms or a multinuclear ring system of up to 30 non-hydrogen atoms;

L is N, O P, or S;

R is hydrogen or a $C_1$ to $C_{30}$ hydrocarbyl or substituted hydrocarbyl;

$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;

each $R^9$ and $R^{13}$ are, independently, hydrogen, a $C_1$ to $C_{30}$ hydrocarbyl or substituted hydrocarbyl;

$R^{10}$, $R^{11}$, $R^{12}$ are, independently, hydrogen or a $C_1$ to $C_{30}$ hydrocarbyl or substituted hydrocarbyl;

each G, is, independently, hydrogen, halogen or $C_1$ to $C_{30}$ substituted or unsubstituted hydrocarbyl;

where any two adjacent R groups may form a single ring of up to 8 non-hydrogen atoms or a multinuclear ring system of up to 30 non-hydrogen atoms; and wherein the alpha olefin produced has at least one more carbon atom than the alkene.

15. The process of claim 14, wherein the triacylglyceride is contacted with alcohol and converted to an fatty acid ester or fatty acid alkyl ester prior to contacting with the catalyst compound.

16. The process of claim 14, wherein the triacylglyceride is contacted with water and converted to a fatty acid prior to contacting with the catalyst compound.

17. A process to produce alpha-olefin comprising contacting an unsaturated fatty acid with an alkene and the catalyst compound of claim 1.

18. A process to produce alpha-olefin comprising contacting a triacylglyceride with the catalyst compound of claim 1.

19. A process to produce alpha-olefin comprising contacting an unsaturated fatty acid ester and or unsaturated fatty acid alkyl ester with an alkene and the catalyst compound of claim 1.

20. The process claim 19, wherein the alpha olefin is a linear alpha-olefin having 4 to 24 carbon atoms.

21. The process of claim 19, wherein the alkene is ethylene, propylene, butene, hexene or octene.

22. The process of claim 19, wherein the fatty acid alkyl ester is a fatty acid methyl ester.

23. A process to produce alpha-olefin comprising contacting a feed material with an alkene and a metathesis catalyst compound represented by the formula:

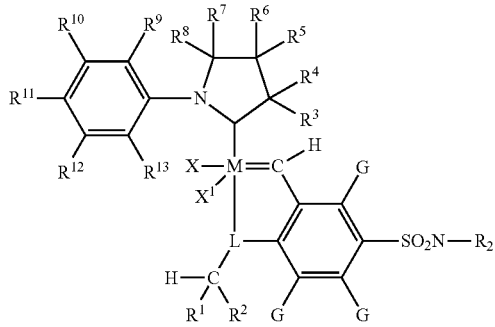

where:
M is a Group 8 metal;
X and $X^1$ are, independently, any anionic ligand, or X and $X^1$ may be joined to form a dianionic group and may form single ring of up to 30 non-hydrogen atoms or a multinuclear ring system of up to 30 non-hydrogen atoms;
L is N, O P, or S;
R is hydrogen or a $C_1$ to $C_{30}$ hydrocarbyl or substituted hydrocarbyl;
$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;
each $R^9$ and $R^{13}$ are, independently, hydrogen, a $C_1$ to $C_{30}$ hydrocarbyl or substituted hydrocarbyl;
$R^{10}$, $R^{11}$, $R^{12}$ are, independently, hydrogen or a $C_1$ to $C_{30}$ hydrocarbyl or substituted hydrocarbyl;
each G, is, independently, hydrogen, halogen or $C_1$ to $C_{30}$ substituted or unsubstituted hydrocarbyl; and
where any two adjacent R groups may form a single ring of up to 8 non-hydrogen atoms or a multinuclear ring system of up to 30 non-hydrogen atoms, wherein the feed material is a triacylglyceride, fatty acid, fatty acid alkyl ester, and/or fatty acid ester derived from biodiesel.

24. The process of claim 19, wherein the alpha-olefin is butene-1, decene-1 and or heptene-1.

25. The process of claim 14, wherein the productivity of the process is at least 200 g of linear alpha-olefin per mmol of catalyst per hour.

26. The process of claim 14, wherein the selectivity of the process is at least 20 wt % linear alpha-olefin, based upon the weight to the material exiting the reactor.

27. The process of claim 14, wherein the turnover number, defined as the moles of alpha olefin formed per mol of catalyst, of the process is at least 10,000.

28. The process of claim 14, wherein the yield, when converting unsaturated fatty acids, unsaturated fatty acid esters, unsaturated fatty acid alkyl esters or mixtures thereof, is 30% or more, said yield being defined as defined as the moles of alpha olefin formed per mol of unsaturated fatty acids, unsaturated fatty acid esters, unsaturated fatty acid alkyl esters or mixtures thereof introduced into the reactor.

29. The process of claim 14, wherein the yield, when converting triacylglycerides as represented in the formula below, is 30% or more, said yield being defined as defined as the moles of alpha olefin formed divided by (the moles of unsaturated $R^a$+moles of unsaturated $R^b$+moles of unsaturated $R^c$) introduced into the reactor,

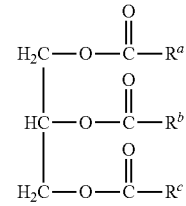

where $R^a$, $R^b$ and $R^c$ each, independently, represent a saturated or unsaturated hydrocarbon chain.

30. The process of claim 28, wherein the yield is 60% or more.

31. A process to produce $C_4$ to $C_{24}$ linear alpha-olefin comprising contacting a feed material with an alkene selected from the group consisting of ethylene, propylene butene, pentene, hexene, heptene, octene, nonene and mixtures thereof and a metathesis catalyst compound represented by the formula:

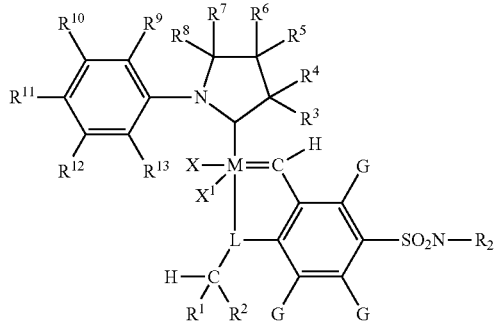

where:
M is a Group 8 metal;
X and $X^1$ are, independently, any anionic ligand, or X and $X^1$ may be joined to form a dianionic group and may form single ring of up to 30 non-hydrogen atoms or a multinuclear ring system of up to 30 non-hydrogen atoms;

L is N, O P, or S;

R is hydrogen or a $C_1$ to $C_{30}$ hydrocarbyl or substituted hydrocarbyl;

$R^1$, $R^2$, $R^3$, $R^4$, $R^5$, $R^6$, $R^7$, and $R^8$ are, independently, hydrogen or a $C_1$ to $C_{30}$ hydrocarbyl or substituted hydrocarbyl;

each $R^9$ and $R^{13}$ are, independently, hydrogen, a $C_1$ to $C_{30}$ hydrocarbyl or substituted hydrocarbyl;

$R^{10}$, $R^{11}$, $R^{12}$ are, independently, hydrogen or a $C_1$ to $C_{30}$ hydrocarbyl or substituted hydrocarbyl;

each G, is, independently, hydrogen, halogen or $C_1$ to $C_{30}$ substituted or unsubstituted hydrocarbyl; and where any two adjacent R groups may form a single ring of up to 8 non-hydrogen atoms or a multinuclear ring system of up to 30 non-hydrogen atoms, wherein the feed material is a triacylglyceride, fatty acid, fatty acid alkyl ester, and/or fatty acid ester derived from seed oil.

32. The process of claim 31, wherein the alkene is ethylene, the alpha olefin is 1-butene, 1-heptene and or 1-decene, and the feed material is a fatty acid methyl ester, and/or fatty acid ester.

* * * * *